(12) United States Patent
Arterburn et al.

(10) Patent No.: US 7,893,106 B2
(45) Date of Patent: Feb. 22, 2011

(54) OXYLIPINS FROM STEARIDONIC ACID AND γ-LINOLENIC ACID AND METHODS OF MAKING AND USING THE SAME

(75) Inventors: Linda Mary Arterburn, Ellicott City, MD (US); William Barclay, Boulder, CO (US); Bindi Dangi, Elkridge, MD (US); James Flatt, Colorado Springs, CO (US); Jung Lee, McLean, VA (US); Dutt Vinjamoori, Chesterfield, MO (US)

(73) Assignee: Martek Biosciences, Corporation, Columbia, MD (US)

( * ) Notice: Subject to any disclaimer, the term of this patent is extended or adjusted under 35 U.S.C. 154(b) by 0 days.

(21) Appl. No.: 11/669,730

(22) Filed: Jan. 31, 2007

(65) Prior Publication Data

US 2007/0248586 A1    Oct. 25, 2007

Related U.S. Application Data

(63) Continuation-in-part of application No. 11/284,790, filed on Nov. 21, 2005.

(60) Provisional application No. 60/763,964, filed on Jan. 31, 2006, provisional application No. 60/629,842, filed on Nov. 19, 2004, provisional application No. 60/729,038, filed on Oct. 21, 2005.

(51) Int. Cl.
*A61K 31/22* (2006.01)
*C07C 57/00* (2006.01)
*C07C 59/00* (2006.01)

(52) U.S. Cl. ................. 514/549; 514/164; 514/171; 514/560; 562/579; 562/512; 562/400; 554/230; 554/224; 554/227

(58) Field of Classification Search ................. 514/164, 514/171, 549, 560; 554/224; 562/400, 512
See application file for complete search history.

(56) References Cited

U.S. PATENT DOCUMENTS 5,102,670 A    4/1992    Abraham et al.

(Continued)

FOREIGN PATENT DOCUMENTS

| CZ | 281096 | 6/1996 |
|---|---|---|
| WO | WO 9933355 | * 7/1999 |
| WO | WO 01/34547 | 5/2001 |

OTHER PUBLICATIONS

Jiang Z.D., et al., Eixosanoids and Other Hydroxylated Fatty Acids fro the marine Alaga Gracilariopsis Lemaneiformis, 1991, Phytochemistry, vol. 30, No. 4, pp. 1187-1190.*

Wheelean et al., Matabolism of Lukotriene B4 in cultured hepatoma cells, Aug. 20, 1995, Archives of Biochemistry ad Biophysics, vol. 321, No. 2, pp. 381-389.*

(Continued)

*Primary Examiner*—Rosalynd Keys
*Assistant Examiner*—Yate' K Cutliff
(74) *Attorney, Agent, or Firm*—Sheridan Ross, P.C.

(57) ABSTRACT

Disclosed are novel oxylipins that are derived from γ-linolenic acid (GLA; 18:3n-6) and stearidonic acid (STA or SDA; 18:4n-3), and methods of making and using such oxylipins. Also disclosed is the use of such oxylipins in therapeutic and nutritional or cosmetic applications, and particularly as anti-inflammatory or anti-neurodegenerative compounds. Also disclosed are The invention novel ways of producing long chain polyunsaturated acid (LCPUFA)-rich oils and compositions that contain enhanced and effective amounts of SDA- and/or GLA-derived oxylipins.

13 Claims, 6 Drawing Sheets

U.S. PATENT DOCUMENTS

| | | | |
|---|---|---|---|
| 5,603,959 | A | 2/1997 | Horrobin et al. |
| 5,955,496 | A | 9/1999 | Hammock et al. |
| 6,174,695 | B1 | 1/2001 | Hammock et al. |
| 6,596,766 | B1 | 7/2003 | Igarashi et al. |
| 6,670,396 | B2 | 12/2003 | Serhan et al. |
| 6,777,211 | B1 * | 8/2004 | Saitoh et al. ............... 435/125 |
| 6,887,901 | B1 | 5/2005 | Serhan |
| 6,949,664 | B2 | 9/2005 | Petasis |
| 7,041,485 | B2 | 5/2006 | Bouarab et al. |
| 7,045,143 | B1 * | 5/2006 | Sawatzki et al. ............ 424/439 |
| 7,154,022 | B2 * | 12/2006 | Howe et al. ................. 800/281 |
| 7,273,624 | B2 | 9/2007 | Rosenberg et al. |
| 2004/0048927 | A1 | 3/2004 | Horrobin |
| 2004/0166130 | A1 | 8/2004 | Filippi et al. |
| 2005/0106603 | A1 | 5/2005 | Onuki et al. |
| 2005/0228047 | A1 | 10/2005 | Petasis |
| 2006/0241088 | A1 | 10/2006 | Arterburn et al. |

OTHER PUBLICATIONS

Kobayashi et al., Important contributin of the methylene part of LTB4 toward binding affinity to the LTB$ receptors and rise in intracellular-free calcium concentration, 1994, Biochimica et Biophysica Acta, vol. 1215(3), pp. 280-284.*

Bergholte et al., Archives of Biochemistry and Biophysics, Sep. 1987, vol. 257, No. 2, pp. 444-450.

Chavis et al., Biochemical and Biophysical Research Communications, vol. 207, No. 1, 1995, pp. 273-279.

Chavis et al., Biochemical Pharmacology, vol. 56, 1998, pp. 535-541.

Chavis et al., J. Exp. Med., Apr. 1996, vol. 183, pp. 1633-1643.

Coffa et al., Lipids, vol. 35, No. 11, 2000, pp. 1195-1204.

Costello et al., Annals of the Rheumatic Diseases, 1992, vol. 51, pp. 1215-1218.

Di Marzo et al., Biochem. J. (1994), vol. 300, pp. 501-507.

Green et al., Lipids, 1990, Viol 25, No. 10, pp. 618-623.

Hamberg, J. Chem. Soc. Perkin Trans., 1993, pp. 3065-3072.

Hong et al., "Novel Docosatrienes and 17S-Resolvins Generated from Docosahexaenoic Acid in Murine Brain, Human Blood, and Glial Cells", The Journal of Biological Chemistry, vol. 278, No. 17, Apr. 25, 2003, pp. 14677-14687.

Jiang et al., Phytochemistry, 1991, vol. 30, No. 4, pp. 1187-1190.

Jubiz et al., Biochemical and Biophysical Research Communications, 1983, vol. 114, No. 2, pp. 855-862.

Knight et al., Biofouling, 1999, vol. 14(3), pp. 213-217.

Knight et al., J. Mar. Biol., Ass. U.K., 2000, vol. 80, pp. 113-117.

Lam et al., "Transformation of 15-Hydroperoxyeicosapentaenoic Acid Into Mono and Dihydroxyeicosapentaenoic Acids by Human Platelets", Life Sciences, 1985, vol. 95, ISSN: 0258-1213 pp. 167-180.

Lam et al., Biochimica et Biophysica Acta, 1987, vol. 917, pp. 398-405.

Maas et al., Proc. Natl. Acad. Sci. USA, May 1983, vol. 80, pagea 2884-2888.

Mancini et al., Helvetica Chimica Acta, 1999, vol. 82, pp. 677-684.

Marcheselli et al., "Novel Docosanoids Inhibit Brain Ischemia-Reperfusion-mediated Leukocyte Infiltration and Pro-inflammatory Gene Expression", The Journal of Biological Chemistry, vol. 278, No. 44, Oct. 31, 2003, pp. 43807-43817.

Milks et al., Metabolism of 4, 7, 10, 13, 16-docosapentaenoic acid by human platelet cyclooxygenase and lipoxygenase, 1985, Biochimica et Biophysica Acta, Lipids and lipid Megabolism, 835(1), Abstract (HCAPLUS).

Mitchell et al. "Inhibition of platelet 12-lipoxygenase by hydroxy-fatty acids", Biochemical Society Transactions, 607th Meeting, London, 1984, pp. 839-841.

Nicolaou et al., J. Am. Chem. Soc., 1984, vol. 106, pp. 5734-5736.

Oliw et al., "Metabolism of polyunsaturated fatty acids by an (n-6)-lipoxygenase associated with human ejaculates", Biochimica et Biophysica Acta, 1002 (1989), pp. 283-291.

Petrich et al., Biochem. J. (1996) vol. 314, pp. 911-916.

Rabinovitch et al., Agents and Actions, 1981, vol. 11, 6/7, pp. 580-583.

Rowley et al., Biochemistry, 1994, vol. 33, pp. 856-863.

Senger et al., The Journal of Biological Chemistry, vol. 280, No. 9, Mar. 4, 1005, pp. 758-7596.

Serhan et al., "Resolvins: A Family of Bioactive Products of Omega-3 Fatty Acid Transformation Circuits Initiated by Aspirin Treatment that Counter Proinflammation Signals", J. Exp. Med., vol. 196, No. 8, Oct. 21, 2002, pp. 1025-1037.

Sirois et al., Prostaglandins, Sep. 1982, vol. 24, No. 3, pp. 405-418.

Sok et al., Korean Biochem. J., 1988, vol. 21, No. 4, pp. 512-518.

Sprecher et al., Prostaglandins, Leukotrienes and Medicine, 1986, vol. 23, pp. 129-134.

Thomas et al., Inflamm Res., 19995, vol. 44, pp. 121-124.

Tori et al., Molecules, 2003, vol. 8, pp. 882-885.

VanRollins et al, "Oxidation of dicoshexaenoic acid by rat liveer microsomes", 1984, Journal of Biological Chemistry, 259(9), Abstract (HCAPLUS).

VanRollins et al., Biocimica et Biophysica Acta, 1985, vol. 833, pp. 272-280.

Woolard et al., Journal of Chromatography, 1984, vol. 306, pp. 1-21.

Yamane et al., Journal of Chromatography, 1992, vol. 579, pp. 25-36.

International Search Report for International (PCT) Patent Application No. PCT/US2005/042462, mailed Aug. 14, 2006.

Written Opinion for International (PCT) Patent Application No. PCT/US2005/042462, mailed Aug. 14, 2006.

International Preliminary Report on Patentability for International (PCT) Patent Application No. PCT/US2005/042462, mailed May 31, 2007.

Official Action for U.S. Appl. No. 11/284,790, mailed Jan. 30, 2008.

Bouarab et al. "The Innate Immunity of a Marine Red Alga Involves Oxyllpins from Both the Eicosanold and Octadecanoid Pathways", Plant Physiology, Jul. 2004, vol. 135, pp. 1838-1848.

International Search Report for International (PCT) Patent Application No. PCT/US07/61397, mailed Apr. 29, 2008.

Written Opinion for International (PCT) Patent Applictaion No. PCT/US07/61397, mailed Apr. 29, 2008.

U.S. Appl. No. 12/357,388, filed Jan. 21, 2009, Dangi.

"Fatty acids—good for the brain, good for Alzheimer disease", vol. 115, No. 10, Oct. 2005, p. 2585.

Arita et al. "Resolvin E1, an endogenous lipid mediator derived from omega-3 eicosapentaenoic acid, protects against 2,4,6-trinitrobenzene sulfonic acid-induced colitis", PNAS May 24, 2005, vol. 102, No. 21, 7671-7676.

Arita et al. "The contributions of aspirin and microbial oxygenase to the biosynthesis of anti-inflammatory resolvins: Novel oxygenase products from x-3 polyunsaturated fatty acids", Biochemical and Biophysical Research Communications 336 (2005), 9 pages.

Arita et al., "Stereochemical assignment, antiinflammatory properties, and receptor for the omega-3 lipid mediator resolvin E1", JEM vol. 201, No. 5, Mar. 7, 2005 713-722.

Bannenberg et al. "Molecular Circuits of Resolution: Formation and Actions of Resolvins and Protectins", The Journal of Immunology, 2005, pp. 4345-4355.

Belayev et al., "Docosahexaenoic Acid Complexed to Albumin Elicits High-Grade Ischemic Neuroprotection", Stroke, Jan. 2005, pp. 118-123.

Butovich "On the Structure, Synthesis and Mechanism of Formation Ofneuroprotectin D1—A Novel Anti-Nflammatory Compound of Docosahexaenoic Acid Family", Department of Ophthalmology, University of Texas Southwestern Medical Center, Dallas, TX 75390-9057, 2005, 17 pages.

Butovich et al. "Novel Oxylipins Formed from Docosahexaenoic Acid by Potato Lipoxygenase-10(S)-Hydroxydocosahexaenoic Acid and 10,20-Dihydroxydocosahexaenoic Acid" Lipids, vol. 40, No. 3, 2005, pp. 249-257.

Chen et al. "Lipid signaling: Sleep, synaptic plasticity, and neuroprotection", Prostaglandins & other Lipid Mediators 77 (2005) 65-76.

Flower et al., "Controlling inflammation: a fat chance?", JEM, vol. 201, No. 5, Mar. 7, 2005 671-674.

Jiang et al., "5-Lipoxygenase-derived oxylipins from the red alga *Rhodymenia pertusa*" Phytochemistry 53 (2000) 129-133.

Kumon et al., "A new labyrinthulid isolate, which solely produces n-6 docosapentaenoic acid", Appl. Microbiol Biotechnol, 2003, vol. 63, pp. 22-28.

Lukiw et al. "A role for docosahexaenoic acid—derived neuroprotectin D1 in neural cell survival and Alzheimer disease", The Journal of Clinical Investigation, vol. 115, No. 10, Oct. 2005, pp. 2774-2783.

Mukherjee et al., "Neuroprotectin D1: A docosahexaenoic acid-derived docosatriene protects human retinal pigment epithelial cells from oxidative stress", PNAS, Jun. 1, 2004, vol. 101, No. 22, pp. 8491-8496.

Napier et al. "The production of very-long-chain PUFA biosynthesis in transgenic plants: towards a sustainable source of fish oils", Proceedings of the Nutrition Society (2005), 64, 387-393.

Robert et al., "Metabolic engineering of Arabidopsis to produce nutritionally important DHA in seed oil", Functional Plant Biology, 2005, 32, pp. 473-479.

Rorrer et al. "Bioreactor seaweed cell culture for production of bioactive oxylipins", Journal of Applied Phycology (Historical Archive), vol. 7, Issue 2, Apr. 1995, pp. 187-198.

Rorrer et al. "Development and Bioreactor Cultivation of a Novel Semidifferentiated Tissue Suspension Derived from the Marine Plant *Acrosiphonia coalita*", Biotechnology and Bioengineering, vol. 49, pp. 559-567 (1996).

Rorrer et al., "Production of Hydroxy Fatty Acids by Cell Suspension Cultures of the Marine Brown Alga Laminaria Saccharina", Phytochemistry, vol. 46, No. 5, 1997, pp. 871-877.

Serhan et al. "Resolvins, docosatrienes, and neuroprotectins, novel omega-3-derived mediators, and their aspirin-triggered endogenous epimers: an overview of their protective roles in catabasis", Prostaglandins & other Lipid Mediators 73 (2004) 155-172.

Simopoulos, A.P., et al. Evolutinary aspects of diet, essential fatty acids and cardiovaxcular disease, 2001, European Heart Journal supplements, 3, (Supplement 0), 08-021.

Official Action for U.S. Appl. No. 11/284,790, mailed Jun. 26, 2009.

VanRollins et al, "Oxidation of dicoshexaenoic acid by rat liveer microsomes", 1984, Journal of Biological Chemistry, vol. 259, No. 9, Issue of May 10, 1984, pp. 5776-5783.

Gardner et al., "Lipoxygenase as a Versatile Biocatalyst", Journal of American Oil Chemist's Society, vol. 73, No. 11, 1986, pp. 1347-1357.

U.S. Appl. No. 12/162,945, filed Jan. 31, 2007, Arterburn et al.

Greiner et al., Lipids, 2003, vol. 38(4), pp. 431-435.

Hoshino et al., Agricultural and Biological Chemistry, 1990, vol. 54(6), pp. 1459-1467.

Karanian, et al., "Inhibitory Effects of n-6 and n-3 Hydroxy Fatty Acids on Thromboxane 9U46619)-Induced Smooth Muscle Contraction", 1994. The Journal of Pharmacology and Experimental Therapeutics, vol. 270, No. 3, pp. 1105-1109.

Moriguchi et al., Journal of Lipid Research, 2001, vol. 42, pp. 419-427.

Official Action for U.S. Appl. No. 11/284,790, mailed Oct. 21, 2008.

International Search Report for International (PCT) Patent Application No. PCT/US08/54456, mailed Aug. 6, 2008.

Written Opinion for International (PCT) Patent Application No. PCT/US08/54456, mailed Aug. 6, 2008.

International Preliminary Report on Patentability for International (PCT) Patent Application No. PCT/US07/61397, mailed Aug. 14, 2008.

International Preliminary Report on Patentability for International (PCT) Patent Application No. PCT/US08/54456, mailed Sep. 3, 2009.

Official Action for U.S. Appl. No. 11/284,790, mailed Dec. 4, 2009.

Eder et al. "The effect of fatty acid composition of rapeseed oil on plasma lipids and oxidative stability of low-density lipoproteins in cholesterol-fed hamsters", Eur. J. Lipid Sci. Technol. 104 (2002) pp. 3-13.

Guerriero et al., "Hydroxyicosatetraenoic, Hydroxyicosapentaenoic, Hydroxydocosapentaenoic, and Hydroxydocosahexaenoic Acids from the Sponge Echinochalina Mollis of the Coral Sea", Journal of Natural Products, vol. 53, No. 1, 1990, pp. 57-61, XP002563390.

Milks et al., Metabolism of 4, 7, 10, 13, 16-docosapentaenoic acid by human platelet cyclooxygenase and lipoxygenase, 1985, Biochimica et Biophysica Acta, Lipids and lipid Megabolism, 835(1),1985, pp. 29-35 (HCAPLUS).

Yergey et al., "High-Performance Liquid Chromatography/Thermospray Mass Spectrometry of Eicosanoids and Novel Oxygenated Metabolites of Docosahexaenoic Acid", Analytical Chemistry, vol. 58, 1986, pp. 1344-1348, XP002563391.

"Chemical and Biological Characterization of Two Omega-6 Docosapentaenoic Acid (DPAn-6)-derived Oxylipins Involved in the Resolution of Inflammation: 17-hydroxy DPAn-6 and 10,17-dihydroxy DPAn-6." Martek Biosciences Corporation. 40 Pages. Oct. 1, 2008.

* cited by examiner

Stearidonic Acid (SDA)

13-hydroxy SDA 6,13-dihydroxy SDA 6-hydroxy SDA 10-hydroxy SDA 7-hydroxy SDA 12-hydroxy SDA 9-hydroxy SDA 13-hydroxy SDA 15-hydroxy SDA 16-hydroxy SDA 6,13-dihydroxy SDA 6,16-dihydroxy SDA 6-hydroxy GLA 10-hydroxy GLA 7-hydroxy GLA 12-hydroxy GLA 9-hydroxy GLA 13-hydroxy GLA 6,13-dihydroxy GLA

OXYLIPINS FROM STEARIDONIC ACID AND γ-LINOLENIC ACID AND METHODS OF MAKING AND USING THE SAME

CROSS-REFERENCE TO RELATED APPLICATIONS

This application claims the benefit of priority under 35 U.S.C. §119(e) from U.S. Provisional Application No. 60/763,964, filed Jan. 31, 2006. This application is also a continuation-in-part of copending U.S. patent application Ser. No. 11/284,790, filed Nov. 21, 2005, which claims the benefit of priority from U.S. Provisional Application Ser. No. 60/629,842, filed Nov. 19, 2004, and from U.S. Provisional Application Ser. No. 60/729,038, filed Oct. 21, 2005. The entire disclosure of each of U.S. Provisional Application No. 60/763,964, U.S. patent application Ser. No. 11/284,790, U.S. Provisional Application Ser. No. 60/629,842, and U.S. Provisional Application Ser. No. 60/729,038 is incorporated herein by reference.

FIELD OF THE INVENTION

This invention generally relates to the use of γ-linolenic acid (GLA; 18:3n-6) and stearidonic acid (STA or SDA; 18:4n-3) as substrates for the production of novel oxylipins, and to the oxylipins produced thereby. The invention further relates to the use of SDA, GLA, and/or the oxylipins derived therefrom, particularly as anti-inflammatory compounds. The invention also relates to novel ways of producing long chain polyunsaturated acid (LCPUFA)-rich oils and compositions that contain enhanced and effective amounts of LCPUFA-derived oxylipins, and particularly, SDA- and GLA-derived oxylipins.

BACKGROUND OF THE INVENTION

Researchers in the 1990s identified hydroxy derivatives of some fatty acids in macroalgae (seaweeds) and described the possible role of these compounds in wound healing and cell signaling in the organisms (Gerwick & Bernart 1993; Gerwick et al 1993; Gerwick 1994). They recognized these compounds to be similar to those produced in the human body through the lipoxygenase pathway. These same researchers also attempted to develop cell suspension cultures of these seaweeds to produce eicosanoids and related oxylipins from the C18 fatty acids, linoleic acid, and linolenic acid, and from arachidonic acid (C20:4n-6) (ARA) in the red, brown and green seaweeds. However, production of seaweed biomass in these cultures systems proved to be very poor (e.g. about 0.6 to 1.0 g/L seaweed biomass after 15 days (Rorrer et al. 1996)) and even direct addition of key fatty acids to the cultures only minimally increased production of oxylipins over that of controls (Rorrer et al. 1997). Additionally, in some cases, the added free fatty acids proved toxic to the cultures (Rorrer et al. 1997). Therefore these systems have only remained academically interesting for producing oxygenated forms of these fatty acids, and studies continue on these C18 and C20 oxylipins in these seaweeds (e.g., Bouarab et al. 2004).

The oxylipins from the long chain omega-6 (n-6 or ω-6 or N6) fatty acid, ARA, have been well studied and are generally considered to be proinflammatory in humans. Oxylipins from the long chain omega-3 (n-3 or ω-3 or N3) fatty acids, however, have generally been found to be anti-inflammatory. In the early 2000's, Serhan and other researchers discovered that hydroxylated forms of two long chain omega-3 polyunsaturated fatty acids (omega-3 LCPUFAs) (i.e., eicosapentaenoic acid (C20:5, n-3) (EPA) and docosahexaenoic acid C22:6, n-3) (DHA)) were made in the human body (Serhan et al. 2004a,b; Bannenberg et al. 2005a,b) They identified pathways whereby the omega-3 LCPUFAs, EPA and DHA, were processed by cyclooxygenases, acetylated cyclooxygenase-2 or by lipoxygenase enzymes, resulting in production of novel mono-, di- and tri-hydroxy derivatives of these fatty acids. The resulting compounds, which were named "resolvins" (because they were involved in the resolution phase of acute inflammation) or docosatrienes (because they were made from docosahexaenoic acid and contain conjugated double bonds), were determined to have strong anti-inflammatory (Arita et al. 2005a,b,c; Flower & Perretti 2005; Hong et al. 2003; Marcjeselli et al. 2003; Ariel et al. 2005), antiproliferative, and neuroprotective (Bazan 2005a,b; Bazan et al. 2005; Belayev et al. 2005; Butovich et al. 2005; Chen & Bazan 2005; Lukiw et al. 2005; Mukherjee et al 2004) properties. These compounds were also noted to have longer half-lives in the human body as compared to other types of eicosanoids.

In the past few years, various patents and patent application publications have described analogs of hydroxy derivatives of ARA, DHA and EPA, the pathways by which they are formed, methods for their synthesis in the laboratory via organic synthetic means or through biogenesis using cyclooxygenase or lipoxygenase enzymes, and use of these hydroxy derivatives as pharmaceutical compounds for the treatment of inflammatory diseases. These patents and publications are summarized briefly below.

U.S. Pat. No. 4,560,514 describes the production of both pro-inflammatory (LX-A) and anti-inflammatory tri-hydroxy lipoxins (LX-B) derived from arachidonic acid (ARA). Use of these compounds in both studying and preventing inflammation (as pharmaceutical compounds) are also described.

U.S. Patent Application Publication No. 2003/0166716 describes the use of lipoxins (derived from ARA) and aspirin-triggered lipoxins in the treatment of asthma and inflammatory airway diseases. Chemical structures of various anti-inflammatory lipoxin analogs are also taught.

U.S. Patent Application Publication No. 2003/0236423 discloses synthetic methods based on organic chemistry for preparing trihydroxy polyunsaturated eicosanoids and their structural analogs including methods for preparing derivatives of these compounds. Uses for these compounds and their derivatives in the treatment of inflammatory conditions or undesired cell proliferation are also discussed.

PCT Publication No. WO 2004/078143 is directed to methods for identifying receptors that interact with di- and tri-hydroxy EPA resolving analogs.

U.S. Patent Application Publication No. 2004/0116408A1 discloses that the interaction of EPA or DHA in the human body with cyclooxygenase-11 (COX2) and an analgesic such as aspirin leads to the formation of di- and tri-hydroxy EPA or DHA compounds with beneficial effects relating to inflammation. It also teaches methods of use and methods of preparing these compounds.

U.S. Patent Application Publication No. 2005/0075398A1 discloses that the docosatriene 10,17S-docosatriene (neuroprotectin D1) appears to have neuroprotective effects in the human body.

PCT Publication No. WO 2005/089744A2 teaches that di- and tri-hydroxy resolvin derivatives of EPA and DHA and stable analogs thereof are beneficial in the treatment of airway diseases and asthma.

U.S. Patent Publication No. 2006/0293288 describes the use of EPA and DHA resolvis for treatment of gastrointestinal diseases.

While the references above describe lipoxins derived from ARA and docosatrienes and resolvins derived from DHA and EPA, as well as various applications of such compounds, there remains a need in the art for alternative ways of delivering the anti-inflammatory benefits and other benefits of these LCPUFA oxylipins (and in particular docosanoids) to consumers other than by providing consumers with combinations of LCPUFA oil and aspirin or by chemically synthesizing these derivatives or their analogs.

Moreover, none of the references above describe methods for making these specific compounds in microbial cultures or plants, nor do they describe methods for increasing the content of these beneficial hydroxy fatty acid derivatives in edible oils. In addition, none of these references describe any hydroxy derivatives from other LCPUFAs, nor do any of these references suggest that that there could be a beneficial role for hydroxy derivatives of any LCPUFAs other than ARA, DHA and EPA.

SUMMARY OF THE INVENTION

One embodiment of the present invention relates to an isolated dihydroxy or trihydroxy oxylipin of stearidonic acid (SDA). In one aspect, the oxylipin is an R- or S-epimer or an R/S epimer (or other combination thereof) of 6,13-dihydroxy SDA or 6,16-dihydroxy SDA, or an analog, derivative or salt thereof.

Another embodiment of the present invention relates to an isolated monohydroxy oxylipin of stearidonic acid (SDA), wherein the oxylipin is an R- or S-epimer or an R/S epimer (or other combination thereof) of an oxylipin selected from the group consisting of: 6-hydroxy SDA, 7-hydroxy SDA, 10-hydroxy SDA, 12-hydroxy SDA, 15-hydroxy SDA and 16-hydroxy SDA or an analog, derivative or salt thereof.

Yet another embodiment of the present invention relates to an isolated dihydroxy or trihydroxy oxylipin of γ-linolenic acid (GLA). In one aspect, the oxylipin is an R- or S-epimer or an R/S epimer (or other combination thereof) of 6,13-dihydroxy GLA, or an analog, derivative or salt thereof.

Another embodiment of the present invention relates to an isolated monohydroxy oxylipin of γ-linolenic acid (GLA), wherein the oxylipin is an R- or S-epimer or an R/S epimer (or other combination thereof) of an oxylipin selected from the group consisting of: 7-hydroxy GLA and, 12-hydroxy GLA, or an analog, derivative or salt thereof.

Another embodiment of the present invention includes a composition comprising at least one of any of the above-described oxylipins or oils. In one aspect, such a composition can also include a compound selected from: SDA, GLA, DPAn-6, DPAn-3, DTAn-6, DHA, EPA, an oxylipin derivative of SDA, an oxylipin derivative of GLA, an oxylipin derivative of DPAn-6, an oxylipin derivative of DPAn-3, an oxylipin derivative of DTAn-3, an oxylipin derivative of DHA and an oxylipin derivative of EPA. Such a composition can include a therapeutic composition, a nutritional composition, or a cosmetic composition. In one aspect, the composition also includes aspirin. In another aspect, the composition also includes at least one agent (one or more agents) selected from: a statin, a non-steroidal anti-inflammatory agent, an antioxidant, and a neuroprotective agent. In one aspect, the composition includes an oil selected from: a microbial oil, a plant seed oil, and an aquatic animal oil.

Yet another embodiment of the invention relates to an oil comprising at least about 10 µg, at least about 20 µg, at least about 50 µg, or at least about 100 µg of at least one oxylipin per gram of oil, wherein the oxylipin is selected from: an oxylipin from SDA and an oxylipin from GLA. In one aspect, the oxylipin is from SDA, which can include, but is not limited to, an R- or S-epimer of an oxylipin selected from: monohydroxy derivatives of SDA, dihydroxy derivatives of SDA, and trihydroxy derivatives of SDA. Such oxylipins include, but are not limited to, an R- or S-epimer or an R/S epimer (or other combination thereof) of an oxylipin selected from: 6-hydroxy SDA, 7-hydroxy SDA, 9-hydroxy SDA, 10-hydroxy SDA, 12-hydroxy SDA, 15-hydroxy SDA, 16-hydroxy SDA, 6,13-dihydroxy SDA, and 6,16-dihydroxy SDA, or an analog, derivative or salt thereof. In another aspect, the oxylipin is from GLA, which can include, but is not limited to, an R- or S-epimer or an R/S epimer (or other combination thereof) of an oxylipin selected from: monohydroxy derivatives of GLA, dihydroxy derivatives of GLA, and trihydroxy derivatives of GLA. Such oxylipins include, but are not limited to, an R- or S-epimer or an R/S epimer (or other combination thereof) of an oxylipin selected from: 6-hydroxy GLA, 7-hydroxy GLA, 9-hydroxy GLA, 12-hydroxy GLA, 13-hydroxy GLA and 6,13-dihydroxy GLA, or an analog, derivative or salt thereof. In one aspect, the oil is selected from: a microbial oil, a plant seed oil, and an aquatic animal oil.

Another embodiment of the invention relates to a composition comprising any one or more of the above-described oils. The composition can include, but is not limited to, a therapeutic composition, a nutritional composition, or a cosmetic composition.

Yet another embodiment of the present invention relates to a composition comprising a long chain polyunsaturated fatty acid (LCPUFA) selected from: SDA and GLA, and a pharmaceutically or nutritionally acceptable carrier. In one aspect, the composition also includes aspirin. In another aspect, the composition also includes an enzyme that catalyzes the production of an oxylipin from the LCPUFA.

Another embodiment of the present invention relates to a method to prevent or reduce at least one symptom of inflammation or neurodegeneration in an individual. The method includes administering to an individual at risk of, diagnosed with, or suspected of having inflammation or neurodegeneration or a condition or disease related thereto, an oxylipin derivative of SDA and/or an oxylipin derivative of GLA, to reduce at least one symptom of inflammation or neurodegeneration in the individual. Also included in the invention is the use of any of an oxylipin derivative of SDA and/or an oxylipin derivative of GLA in the preparation of a medicament for the prevention or reduction of at least one symptom of inflammation or neurodegeneration in an individual. In preferred aspects of these embodiments of the invention, the oxylipin derivative is effective: to reduce the production of tumor necrosis factor-α (TNF-α), to reduce the migration of neutrophils and macrophages into a site of inflammation, to reduce interleukin-1β (IL-1β) production in the individual, and/or to reduce macrophage chemotactic protein-1 (MCP-1) in the individual.

In one aspect of the above-embodiments, the method also includes administering at least one long chain fatty acid and/or at least one oxylipin derivative thereof to the individual, or the inclusion of such long chain fatty acid in the medicament. Such long chain fatty acids include, but are not limited to, GLA, SDA, DHA, EPA, DPAn-6, DTAn-6, and DPAn-3. In one aspect, the long chain fatty acid is provided in one of the following forms: as triglyceride containing the long chain fatty acid, as a phospholipid containing the long chain fatty acid, as a free fatty acid, or as an ethyl or methyl ester of the long chain fatty acid.

In one aspect of the above embodiments, the oxylipin derivative of SDA or GLA is provided in the form of a microbial oil, an animal oil, a plant oil, or from a microbial, animal or plant oil that has been derived from a microbe, an animal, or an oil seed plant, respectively, that has been genetically modified to produce long chain polyunsaturated fatty acids. In one aspect, the oxylipin derivative is produced from an enzymatic conversion of SDA or GLA to its oxylipin derivative. In one aspect, the oxylipin derivative is chemically synthesized de novo.

In one aspect of the above embodiments, the oxylipin derivative is selected from: R-epimers of the monohydroxy products of SDA, S-epimers of the monohydroxy product of SDA, R-epimers of the monohydroxy products of GLA, S-epimers of the monohydroxy product of GLA, R-epimers of the dihydroxy products of SDA, S-epimers of dihydroxy products of SDA, R-epimers of the dihydroxy products of GLA, S-epimers of dihydroxy products of GLA, R-epimers of the trihydroxy products of SDA, S-epimers of the trihydroxy products of SDA, R-epimers of the trihydroxy products of GLA, and S-epimers of the trihydroxy products of GLA. In one aspect, the oxylipin derivative is an R- or S-epimer or an R/S epimer (or other combination thereof) of an oxylipin selected from: 6-hydroxy SDA; 7-hydroxy SDA; 9-hydroxy SDA; 10-hydroxy SDA; 12-hydroxy SDA; 15-hydroxy SDA; 16-hydroxy SDA; 6,13-dihydroxy SDA; 6,16-dihydroxy SDA; 6-hydroxy GLA; 7-hydroxy GLA; 9-hydroxy GLA; 12-hydroxy GLA; 13-hydroxy GLA; and 6,13-dihydroxy GLA; or an analog, derivative or salt thereof.

In another aspect of the above embodiments, the method further comprises administering DPAn-6 or an oxylipin derivative thereof and/or DPAn-3 or an oxylipin derivative thereof, or the medicament further comprises such agents.

In another aspect of the above embodiments, the method further comprises administering aspirin to the individual, or including asprin in the medicament.

In another aspect of the above embodiments, the method further comprises administering at least one agent selected from: a statin, a non-steroidal anti-inflammatory agent, an antioxidant, and a neuroprotective agent, or the medicament further includes one or more of such agents.

Yet another embodiment of the present invention relates to a method to produce oxylipin derivatives of SDA or GLA. The method includes the step of chemically synthesizing an oxylipin derivative of SDA or an oxylipin derivative of GLA, wherein the oxylipin derivative is an R- or S-epimer or an R/S epimer (or other combination thereof) of an oxylipin selected from: 6-hydroxy SDA; 7-hydroxy SDA; 9-hydroxy SDA; 10-hydroxy SDA; 12-hydroxy SDA; 6,13-dihydroxy SDA; 6-hydroxy GLA; 7-hydroxy GLA; 9-hydroxy GLA; 12-hydroxy GLA; 13-hydroxy GLA; and 6,13-dihydroxy GLA.

Another embodiment of the present invention relates to a method to produce oxylipin derivatives of SDA or GLA, comprising catalytically producing the oxylipin derivatives by contacting an SDA substrate or a GLA substrate with an enzyme that catalyzes the production of the oxylipin derivatives from said SDA substrate or said GLA substrate.

Yet another embodiment of the invention relates to a method to produce oxylipin derivatives of SDA or GLA, comprising culturing SDA- or GLA-producing microorganisms or growing SDA- or GLA-producing plants that have been genetically modified to overexpress an enzyme that catalyzes the production of the oxylipin derivatives from SDA or GLA, to produce said oxylipin derivatives. In another aspect, the SDA- or GLA-producing microorganisms or SDA- or GLA-producing plants have been genetically modified to produce the SDA or GLA. In one aspect, the SDA- or GLA-producing microorganisms or the SDA- or GLA-producing plants endogenously produce the SDA or GLA.

Yet another embodiment of the invention relates to a method to produce oxylipin derivatives of SDA or GLA, comprising contacting SDA or GLA produced by SDA- or GLA-producing microorganisms, SDA- or GLA-producing plants, or SDA- or GLA-producing animals, with an enzyme that catalyzes the conversion of said SDA or GLA to oxylipin derivatives thereof. In one aspect, the SDA- or GLA-producing microorganisms or SDA- or GLA-producing plants have been genetically modified to produce SDA or GLA. In one aspect, the SDA- or GLA-producing microorganisms or the SDA- or GLA-producing plants endogenously produce SDA or GLA.

In any of the above-described methods to produce, the enzyme can include, but is not limited to: a lipoxygenase, a cyclooxygenase, and a cytochrome P450 enzyme. In one aspect, the enzyme is selected from: 12-lipoxygenase, 5-lipoxygenase, 15-lipoxygenase, cyclooxygenase-2, hemoglobin alpha 1, hemoglobin beta, hemoglobin gamma A, CYP4A11, CYP4B1, CYP4F11, CYP4F12, CYP4F2, CYP4F3, CYP4F8, CYP4V2, CYP4X1, CYP41, CYP2J2, CYP2C8, thromboxane A synthase 1, prostaglandin 12 synthase, and prostacyclin synthase.

Another embodiment of the invention relates to a method to enrich an oil for the presence of at least one oxylipin derived from SDA or GLA or stabilize said oxylipin in the oil, comprising culturing an SDA- or GLA-producing microorganism with a compound that enhances the enzymatic activity of an enzyme that catalyzes the conversion of the SDA or GLA to oxylipins. In one aspect, the compound stimulates expression of the enzyme. In another aspect, the compound enhances or initiates autooxidation of the LCPUFAs. In one aspect, the compound is acetosalicylic acid. In another aspect, the method additionally includes recovering and purifying the oxylipins. In one aspect, the oxylipins are further processed and recovered as derivatives of the oxylipins or salts thereof.

Yet another embodiment of the invention relates to a method to enrich an oil for the presence of at least one oxylipin derived from SDA or GLA or stabilize said oxylipin in the oil, comprising rupturing microbes or plant oil seeds in the presence of an enzyme that catalyzes the conversion of the SDA or GLA to oxylipins, wherein the microbes and plant oil seeds produce at least one LCPUFA selected from the group consisting of SDA and GLA. In one aspect, the enzyme is selected from the group consisting of a lipoxygenase, a cyclooxygenase, and a cytochrome P450 enzyme. In one aspect, the method further includes recovering and purifying the oxylipins. In this aspect, the oxylipins can be further processed and recovered as derivatives of the oxylipins or salts thereof.

Another embodiment of the invention relates to a method to process an oil containing oxylipin derivatives of SDA or GLA, comprising the steps of: (a) recovering an oil containing oxylipin derivatives of SDA and/or GLA produced by a microbial, plant or animal source; and (b) refining the oil using a process that minimizes the removal of free fatty acids from the oil to produce an oil that retains oxylipin derivatives of the SDA and/or GLA. In one aspect, the animal is an aquatic animal or a fish. In another aspect, the plant is an oil seed plant. In one aspect, the microbial source is a fungus or an algae.

In one aspect of the method to process an oil, the step of refining comprises extraction of the oil with an alcohol, an alcohol:water mixture, or organic solvent. In one aspect, the step of refining comprises extraction of the oil with a nonpolar organic solvent. In one aspect, the step of refining comprises extraction of the oil with an alcohol or an alcohol:

water mixture. The step of refining can further include chill filtering, bleaching, further chill filtering and deodorizing of the oil. In another aspect, the step of refining can include bleaching and deodorizing the oil, in the absence of chill filtering steps. In another aspect, the step of refining further comprises deodorizing the oil, in the absence of chill filtering or bleaching steps. In yet another aspect, the method further includes adding an antioxidant to the oil. In yet another aspect, the step of refining comprises preparing the oil as an emulsion.

In one aspect of the method to process an oil, the oil is further processed by contact with an enzyme that catalyzes the conversion of SDA or GLA to oxylipins. Such an enzyme can include, but is not limited to, a lipoxygenase, a cyclooxygenase, and a cytochrome P450 enzyme. In one aspect, such an enzyme is immobilized on a substrate.

In one aspect, the method to process an oil further includes separating the oxylipin derivatives from the SDA and GLA in the oil. Separation steps can include, but are not limited to, chromatography. In one aspect, the method further includes adding the separated oxylipin derivatives to an oil or composition.

Yet another embodiment of the invention relates to a method to process an oil containing oxylipin derivatives of SDA or GLA, comprising: (a) recovering an oil containing oxylipin derivatives of SDA or GLA produced by a microbial, plant or animal source; (b) refining the oil; and (c) separating SDA oxylipins or GLA oxylipins from SDA or GLA in the oil. In one aspect, this method further includes, prior to step (c), a step of converting SDA or GLA in the oil to SDA or GLA oxylipins, respectively, by a chemical or biological process. In one aspect, the method further includes adding said separated oxylipins derivatives to a product.

Another embodiment of the invention relates to an organism comprising a classical fatty acid synthase pathway for the production of a long chain fatty acid selected from: SDA and GLA, wherein the organism has been genetically transformed to express an enzyme that converts the SDA or GLA to an oxylipin. In one aspect, the organism is selected from plants and microorganisms. In one aspect, the organism is an oil seed plant that has been genetically modified to produce the long chain fatty acid. In another aspect, the organism is a microorganism. In one aspect, the enzyme is selected from the group consisting of a lipoxygenase, a cyclooxygenase, and a cytochrome P450 enzyme.

BRIEF DESCRIPTION OF THE FIGURES OF THE INVENTION

DETAILED DESCRIPTION OF THE INVENTION

Figure 1:
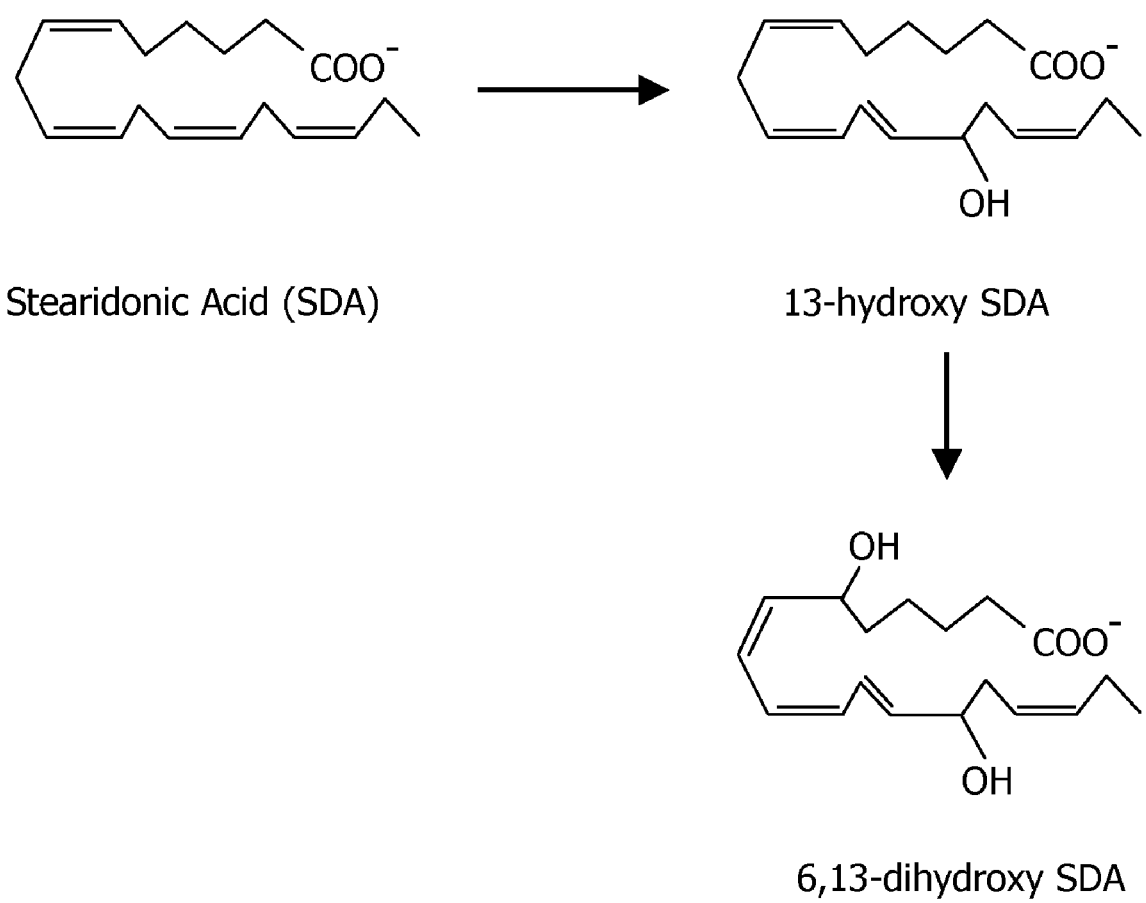
FIG. 1 depicts the structures of the major mono- and dihydroxy products of the reaction of SDA with 15-lipoxygenase.

Recognizing the need in the art for novel anti-inflammatory compounds and for alternative ways of providing known anti-inflammatory compounds, such as the lipoxins, resolvins and docosatrienes described above, the present inventors have made several interrelated discoveries that have resulted in the provision of novel anti-inflammatory reagents and improved compositions for use in anti-inflammation applications.

First, the present invention relates to the discovery by the present inventors that the long chain omega-6 fatty acid, γ-linolenic acid (GLA; 18:3n-6) and the long chain omega-3 fatty acid, stearidonic acid (STA or SDA; 18:4n-3), are substrates for the production of novel compounds referred to generally herein as LCPUFA oxylipins, and more particularly referred to as SDA-derived oxylipins (oxylipins produced from or derived from the knowledge of the structure of SDA) and GLA-derived oxylipins (oxylipins produced from or derived from the knowledge of the structure of GLA), including mono-, di-, and tri-hydroxy derivatives of such oxylipins. The terms "oxylipin" as used herein is defined and described in detail below. According to the present invention, SDA will generally be used to abbreviate "stearidonic acid", although the term STA is also used in the art and is also acceptable for use herein. The present inventors, without being bound by theory, believe that SDA and GLA and the oxylipin derivatives thereof can serve, like the long chain omega-3 fatty acids DHA and EPA and their oxylipin derivatives, as potent anti-inflammatory agents. Therefore, in one embodiment, the present invention provides novel oxylipins derived from SDA and GLA, and derivatives and analogs thereof, as well as methods for the production and use of such oxylipins as anti-inflammatory compounds and nutritional/health supplements. The present invention also provides the use of these LCPUFAs (SDA and GLA) themselves as novel anti-inflammatory compounds (e.g., as a precursor for the oxylipins or as an agent with intrinsic anti-inflammatory activity).

The inventors have discovered that the unique structure of SDA and GLA will allow these LCPUFAs to be converted into a variety of oxylipin derivatives, including di- and tri-hydroxy derivatives, as well as novel mono-hydroxy derivatives, that are similar to DHA oxylipin derivatives known as docosatrienes or resolving. The inventors further propose herein the surprising discovery that oxylipin derivatives of SDA and GLA are new, potent, anti-inflammatory agents.

Prior to the present invention, it was not recognized that the oxylipins synthesized from SDA and GLA have unique properties, especially with regard to inflammation. In particular, and without being bound by theory, the present inventors believe that SDA and GLA and oxylipin derivatives thereof will have at least some anti-inflammatory properties or inflammation regulatory properties, such as those described for DHA, EPA, or the oxylipin derivatives of those LCPUFAs, and in U.S. Patent Publication No. 2006/0241088, for various docosanoids and the LCPUFAs from which they were derived. Combinations of SDA and GLA and/or oxylipin derivatives thereof with DHA or EPA and/or oxylipin derivatives thereof (and particularly with DHA and/or oxylipin derivatives thereof) will provide a greater benefit in nutritional applications (e.g., any applications of the invention directed to the provision of nutrients and nutritional agents to maintain, stabilize, enhance, strengthen, or improve the health of an individual or the organic process by which an organism assimilates and uses food and liquids for functioning, growth and maintenance, and which includes nutraceutical applications), therapeutic applications (e.g., any applications of the invention directed to prevention, treatment, management, healing, alleviation and/or cure of a disease or condition that is a deviation from the health of an individual) and other applications (e.g., cosmetic) than that provided by DHA, EPA and/or oxylipin derivatives thereof alone. In addition, SDA and GLA and/or the oxylipin derivatives thereof can also be combined with any one or more of DPAn-6, DPAn-3, or DTAn-6 and/or the oxylipin derivatives of these LC-PUFAs (described in detail in U.S. Patent Publication No. 2006/0241088, incorporated herein by reference in its entirety), alone or in further combination with DHA, EPA and/or the oxylipin derivatives thereof, for use in any of the nutritional applications, therapeutic applications or other applications provided herein.

As described in U.S. Patent Publication No. 2006/0241088, supra, the inventors were the first to recognize that the enzymes forming the oxylipins such as the previously described docosatrienes and resolvins derived from DHA did not discriminate between the (n-6) and (n-3) 22-carbon fatty acids as substrates because of the presence of the particular double bonds in the same location in these molecules. In fact, the inventors were the first to discover that C22n-6 fatty acids are preferred substrates for these enzymes. The inventors were also the first to recognize that oxylipins from DPAn-6 have strong anti-inflammatory activity, and that oils containing both DHA and DPAn-6 have more anti-inflammatory benefits than oils containing DHA alone. The inventors are now believed to be the first to discover that the LCPUFAs, SDA and GLA, also serve as substrates for the enzymes that were previously described for DHA to form a variety of novel oxylipins, including mono-, di- and trihydroxy oxylipins, and are further believed to be the first to propose the use of these oxylipins, as well as a few previously described monohydroxy oxylipins of SDA and GLA, for the regulation of inflammation, and to propose that such oxylipins can be enriched or enhanced in various oils, organisms (including plants, animals and microorganisms) and compositions.

In another embodiment of the invention, the present inventors have also discovered ways of producing LCPUFA-rich oils that also contain enhanced and effective amounts of the novel oxylipins of the present invention. These LCPUFA-rich oils can be used in nutritional (including nutraceutical), cosmetic and/or pharmaceutical (including therapeutic) applications to deliver the immediate anti-inflammatory/neuroprotective action(s) of the hydroxy-LCPUFA derivatives along with the inherent long-term benefits of the LCPUFAs themselves.

The present inventors further describe herein the provision of oils enriched in LCPUFA oxylipins of the invention (SDA- and GLA-derived oxylipins), as compositions that are of great benefit to human nutrition and health and that provide an alternative to the provision of chemically synthesized oxylipin analogs or to oils containing inadequate amounts of LCPUFA oxylipins. This aspect of the invention is provided through enriching oils in these oxylipins, as well as through alternative ways to process SDA- and GLA-derived oxylipin-containing oils to further enrich and enhance the SDA- and GLA-derived oxylipin content of the oils, thereby significantly enhancing their SDA- and GLA-derived oxylipin levels over those found in conventionally produced/processed LCPUFA oils containing SDA and/or GLA.

In addition, the present inventors have discovered di- and trihydroxy oxylipins that are produced from SDA and GLA, as well as novel monohydroxy oxylipins, and these oxylipins can now be chemically or biogenically produced and used as crude, semi-pure or pure compounds in a variety of compositions and formulations, or even added to oils, such as LCPUFA- or LCPUFA-oxylipin-containing oils, to enhance or supplement the natural oxylipins in such oils. Such compounds can also serve as lead compounds for the production of additional active analogs of these oxylipins in the design and production of nutritional agents and therapeutic drugs.

General Definitions

For the purposes of this application, long chain polyunsaturated fatty acids (LCPUFAs) are defined as fatty acids of at least 18 and more carbon chain length, including fatty acids of 20 or more carbon chain length, containing 2 or more double bonds. LCPUFAs of the omega-6 series include: linoleic acid (LA, 18:2n-6), γ-linolenic acid (GLA; 18:3n-6), di-homo-gammalinoleic acid (C20:3n-6), arachidonic acid (C20:4n-6), docosatetraenoic acid or adrenic acid (C22:4n-6), and docosapentaenoic acid (C22:5n-6). The LCPUFAs of the omega-3 series include: α-linolenic acid (ALA, 18:3n-3), stearidonic acid (STA or SDA; 18:4n-3), eicosatrienoic acid (C20:3n-3), eicosatetraenoic acid (C20:4n-3), eicosapentaenoic acid (C20:5n-3), docosapentaenoic acid (C22:5n-3), and docosahexaenoic acid (C22:6n-3). The LCPUFAs also include fatty acids with greater than 22 carbons and 4 or more double bonds including, but not limited to, C24:6(n-3) and C28:8(n-3).

The terms "polyunsaturated fatty acid" and "PUFA" include not only the free fatty acid form, but other forms as well, such as the triacylglycerol (TAG) form, the phospholipid (PL) form and other esterified forms.

As used herein, the term "lipid" includes phospholipids; free fatty acids; esters of fatty acids; triacylglycerols; diacylglycerides; monoacylglycerides; lysophospholipids; soaps; phosphatides; sterols and sterol esters; carotenoids; xanthophylls (e.g., oxycarotenoids); hydrocarbons; and other lipids known to one of ordinary skill in the art.

For the purposes of this application, "oxylipins" are defined as biologically active, oxygenated derivatives of polyunsaturated fatty acids, formed by oxidative metabolism of polyunsaturated fatty acids. Oxylipins that are formed via the lipoxygenase pathway are called lipoxins. Oxylipins that are formed via the cyclooxygenase pathway are called prostanoids. Oxylipins formed from the 18 carbon fatty acid, stearidonic acid (SDA) are called SDA-derived oxylipins. Oxylipins formed from the 18 carbon fatty acid, γ-linolenic acid (GLA) are called GLA-derived oxylipins. Oxylipins formed from 20 carbon fatty acids (arachidonic acid and eicosapentaenoic acid) are called eicosanoids. Eicosanoids include prostaglandins, leukotrienes and thromboxanes. They are formed either via the lipoxygenase pathway (leukotrienes) or via the cyclooxygenase pathway (prostaglandins, prostacyclin, thromboxanes). Oxylipins formed from 22 carbon fatty acids (docosapentaenoic acid (n-6 or n-3), docosahexaenoic acid and docosatetraenoic acid) are called docosanoids. Specific examples of the GLA-derived and SDA-derived oxylipins are described herein. Specific examples of other oxylipins described above can be found in U.S. Patent Publication No. 2006/0241088, supra. General reference to an oxylipin described herein is intended to encompass the derivatives and analogs of a specified oxylipin compound.

As used herein, the term "analog" refers to a chemical compound that is structurally similar to another compound but differs slightly in composition (as in the replacement of one atom by an atom of a different element or in the presence of a particular functional group, or the replacement of one functional group by another functional group) (see detailed discussion of analogs of the present invention below).

As used herein, the term "derivative", when used to describe a compound of the present invention, means that at least one hydrogen bound to the unsubstituted compound is replaced with a different atom or a chemical moiety (see detailed discussion of derivatives of the present invention below).

In general, the term "biologically active" indicates that a compound has at least one detectable activity that has an effect on the metabolic or other processes of a cell or organism, as measured or observed in vivo (i.e., in a natural physiological environment) or in vitro (i.e., under laboratory conditions).

The oxygenated derivatives (oxylipins) of long chain polyunsaturated fatty acids (LCPUFAs) include mono-, di-, tri-, tetra-, and penta-hydroxy derivatives of the LCPUFAs, and also include the free, esterified, peroxy and epoxy forms of these derivatives. These mono-, di-, tri-, tetra-, and penta-hydroxy derivatives of LCPUFAs are those derivatives that contain 3, 4 or more double bonds, generally at least two of which are conjugated, and one or more non-carboxy, hydroxyl groups. Preferably, these derivatives contain 4-6 double bonds and at least 1-3 non-carboxy, hydroxyl groups, and more preferably, 2 or more non-carboxy, hydroxyl groups.

Oxygenated derivatives of the omega-3 fatty acids EPA and DHA, catalyzed by lipoxygenase or cyclo-oxygenase enzymes, including acetylated forms of cyclooxygenase 2 (COX2), which are capable of down regulating or resolving inflammatory processes, are commonly referred to as "resolvins", which is a coined term (neologism) that is functional in nature. The "docosatrienes" are a subclass of oxylipins derived from DHA and contain three conjugated double bonds. "Protectin" is another coined functional term for hydroxy derivatives of the omega-3 fatty acid DHA that have a neuroprotective effect.

According to the present invention, the term "docosanoid" specifically refers to any oxygenated derivatives (oxylipins) of any 22-carbon LCPUFA (e.g., DHA, DPAn-6, DPAn-3, or DTAn-6). The structures of such derivatives are described in detail in U.S. Patent Publication No. 2006/0241088, supra. It is noted that while the present inventors recognize that the novel oxylipin derivatives (docosanoids) described in U.S. Patent Publication No. 2006/0241088, supra, that are derived from DPAn-6, DPAn-3 and DTAn-6 might also be considered to be "resolvins" or "protectins" based on similar functional attributes of such oxylipins, for the purposes herein, it is preferred that such oxylipins be generally referenced using the term "docosanoid", which provides a clear structural definition of such compounds.

According to the present invention, the term "SDA-derived oxylipin" specifically refers to any oxygenated derivatives (oxylipins) of SDA. The structures of such derivatives are described in detail herein. The term "GLA-derived oxylipin" specifically refers to any oxygenated derivatives (oxylipins) of GLA. The structures of such derivatives are also described in detail herein. The di- and trihydroxy oxylipins from SDA and GLA, and some of the monohydroxy oxylipins from SDA and GLA disclosed herein, have never before been described, to the best of the present inventors' knowledge. As with the docosanoids described above, while the present inventors recognize that the novel oxylipin derivatives of the present invention that are derived from SDA and GLA might also be considered to be "resolvins" or "protectins" based on similar functional attributes of such oxylipins, for the purposes of this invention, it is preferred that the novel oxylipins of the present invention be generally referenced using the term "SDA-derived oxylipin" or "GLA-derived oxylipin", which provides a clear structural definition of such compounds.

Oxylipins Useful in the Present Invention

One embodiment of the present invention relates to novel oxylipins derived from SDA or GLA, and any analogs or derivatives of such oxylipins, including any compositions or formulations or products containing such oxylipins or analogs or derivatives thereof, as well as oils or other compositions or formulations or products that have been enriched by any method for any LCPUFA oxylipin or analogs or derivatives thereof, and particularly for any oxylipin derived from SDA or GLA. The present invention also relates to any oils or other compositions or formulations or products in which such oxylipins (any oxylipin derived from SDA or GLA) are stabilized or retained in the oils or compositions to improve the quantity, quality or stability of the oxylipin in the oil or composition, and/or to improve the absorption, bioavailability, and/or efficacy of the oxylipins contained in oils or compositions.

The present invention provides novel oxylipins derived from SDA and GLA, including analogs or derivatives thereof, which can be enriched in various oils and compositions, preferably using the methods and processes described herein, or which can be produced and if desired, isolated or purified, by a variety of biological or chemical methods, including by de novo production, for use in any therapeutic, nutritional (including nutraceutical), cosmetic, or other application as described herein. Therefore, the present invention encompasses isolated, semi-purified and purified oxylipins as described herein, as well as sources of oxylipins including synthesized and natural sources (e.g., oils or plants and portions thereof), and includes any source that has been enriched for the presence of an oxylipin useful in the present invention by genetic, biological or chemical methods, or by processing steps as described herein.

In general, oxylipins can have either pro-inflammatory or anti-inflammatory properties. According to the present invention, pro-inflammatory properties are properties (characteristics, activities, functions) that enhance inflammation in a cell, tissue or organism, and anti-inflammatory properties are properties that inhibit such inflammation. Inflammation in cells, tissues and/or organisms can be identified by a variety of characteristics including, but not limited to, the production of "proinflammatory" cytokines (e.g., interleukin-1α (IL-1α), IL-1β, tumor necrosis factor-α (TNFβ), IL-6, IL-8, IL-12, macrophage inflammatory protein-1 (MIP-1α), macrophage chemotactic protein-1 (MCP-1; also known as macrophage/monocyte chemotactic and activating factor or monocyte chemoattractant protein-1) and interferon-γ (IFN-γ)), eicosanoid production, histamine production, bradykinin production, prostaglandin production, leukotriene production, fever, edema or other swelling, and accumulation of cellular mediators (e.g., neutrophils, macrophages, lymphocytes, etc.) at the site of inflammation.

In one embodiment, oxylipins useful in the present invention are those having anti-inflammatory properties, such as those derived from DHA, EPA, DPAn-6, DPAn-3, and DTAn-6, as well as SDA and GLA. Other important bioactive properties of oxylipins include, but are not limited to, anti-proliferative activity, antioxidant activity, neuroprotective and/or vasoregulatory activity. These properties are also preferred properties of oxylipins useful in the present invention, and are preferably characteristic of oxylipins derived from DHA, EPA, DPAn-6, DTAn-6, DPAn-3, SDA and GLA. In another embodiment, oxylipins of the present invention include any oxylipins derived from SDA or GLA, regardless of the particular functional properties of the oxylipin (e.g., some oxylipins may be pro-inflammatory or have other properties that are useful in other applications), and particularly include the di- and trihydroxy oxylipins of SDA and GLA described herein, as well as the novel monohydroxy oxylipins from SDA and GLA described herein. Preferred oxylipins derived from SDA and GLA include those that provide a nutritional and/or therapeutic benefit, and more preferably, have anti-inflammatory activity, anti-proliferative activity, antioxidant activity, and/or neuroprotective activity.

EPA-Derived Oxylipins

Oxylipins derived from EPA that are useful in the present invention include, but are not limited to: 15-epi-lipoxin A4 (5S,6R,15R-trihydroxy eicosatetraenoic acid) and its intermediate 15R-hydroxy eicosapentaenoic acid (15R-HEPE); Resolvin E1 (5,12,18-trihydroxy EPA) and its intermediates 5,6-epoxy, 18R-hydroxy-EPE, and 5S-hydro(peroxy), 18R-hydroxy-EPE, and 18R-hydroxy-EPE (18R-HEPE); and Resolvin E2 (5S,18R-dihydroxy-EPE or 5S,18R-diHEPE) and its intermediates. See U.S. Patent Publication No. 2006/0241088, supra for structures of these EPA derivatives. EPA-derived oxylipins are also described in detail in Serhan (2005), which is incorporated herein by reference in its entirety.

DHA-Derived Oxylipins

Oxylipins derived from DHA that are useful in the present invention include, but are not limited to: Resolvin D1 (7,8,17R-trihydroxy DHA) and Resolvin D2 (7,16,17R-trihydroxy DHA) along with their S-epimers and their intermediates including: 17S/R-hydroperoxy DHA, and 7S-hydroperoxy,17S/R-OH-DHA, and 7(8)-epoxy-17S/R-OH-DHA; Resolvin D4 (4,5,17R-trihydroxy DHA) and Resolvin D3 (4,11,17R trihydroxy DHA) along with their S-epimers and their intermediates including 17S/R-hydroperoxy DHA, and 4S-hydroperoxy,17S/R-OH DHA and 4(5)-epoxy-17S/R-OH DHA; and Neuroprotectin D1 (10,17S-docosatriene, protectin D1) along with its R epimer and their intermediates including the dihydroxy product 16,17-epoxy-docosatriene (16,17-epoxy-DT) and the hydroperoxy product 17S-hydroperoxy DHA; Resolvin D5 (7S,17S-dihydroxy DHA) and Resolvin D6 and their hydroxyl containing intermediates; and epoxide derivatives 7,8 epoxy DPA, 10,11-epoxy DPA, 13,14-epoxy DPA, and 19,20-epoxy DPA and dihydroxy derivative 13,14-dihydroxy docosapentaenoic acid; other mono-hydroxy DHA derivatives, including the R and S epimers of 7-hydroxy DHA, 10-hydroxy DHA, 11-hydroxy DHA, 13-hydroxy DHA, 14-hydroxy DHA, 16-hydroxy DHA and 17-hydroxy DHA; and other dihydroxy DHA derivatives, including the R and S epimers of 10,20-dihydroxy DHA, 7,14-dihydroxy DHA and 8,14-dihydroxy DHA. See U.S. Patent Publication No. 2006/0241088, supra for descriptions and structures of these DHA derivatives. DHA-derived oxylipins are also described in detail in Serhan (2005) and Ye et al (2002), which are incorporated herein by reference in its entirety.

DPAn-6-, DTAn-6- and DPAn-3-Derived Oxylipins and Other Novel Docosanoids from C22 Fatty Acids Oxylipins useful in the present invention can be derived from DPAn-6, DTAn-6, or DPA-n-3, or other C22 PUFAs, and have been described in detail in U.S. Patent Publication No. 2006/0241088, supra.

a) DPAn-6-Derived Oxylipins

DPAn-6-derived oxylipins (also referred to as oxylipins, or more particularly, docosanoids, from DPAn-6) include but are not limited to, any R- or S-epimer of any monohydroxy, dihydroxy, trihydroxy, or multi-hydroxy derivative of DPAn-6, and can include hydroxy derivatizations at any carbon that forms a carbon-carbon double bond in DPAn-6. Some exemplary, novel DPAn-6 derived oxylipins of the present invention include, but are not limited to: the R- and S-epimers of the monohydroxy products of DPAn-6, including 7-hydroxy DPAn-6,8-hydroxy DPAn-6,10-hydroxy DPAn-6,11-hydroxy DPAn-6,13-hydroxy DPAn-6,14-hydroxy DPAn-6, and 17-hydroxy DPAn-6 (most particularly 17-hydroxy DPAn-6); the R and S epimers of the dihydroxy derivatives of DPAn-6, including 7,17-dihydroxy DPAn-6, 10,17-dihydroxy DPAn-6, 13,17-dihydroxy DPAn-6, 7,14-dihydroxy DPAn-6, 8,14-dihydroxy DPAn-6, 16,17-dihydroxy DPAn-6, and 4,5-dihydroxy DPAn-6 (most particularly 10,17-dihydroxy DPAn-6); and tri-hydroxy derivatives of DPAn-6, including R and S epimers of 7,16,17-trihydroxy DPAn-6 and 4,5,17-trihydroxy DPAn-6. Structures of the DPAn-6 oxylipins are described and/or shown in U.S. Patent Publication No. 2006/0241088, supra.

b) DPAn-3-Derived Oxylipins

DPAn-3-derived oxylipins (also referred to as oxylipins, or more particularly, docosanoids, from DPAn-3) include but are not limited to, any R- or S-epimer of any monohydroxy, dihydroxy, trihydroxy, or multi-hydroxy derivative of DPAn-3, and can include hydroxy derivatizations at any carbon that forms a carbon-carbon double bond in DPAn-3. Some exemplary, novel DPAn-3 derived oxylipins of the present invention include, but are not limited to: the R- and S-epimers of the monohydroxy products of DPAn-3, including 7-hydroxy DPAn-3,10-hydroxy DPAn-3,11-hydroxy DPAn-3,13-hydroxy DPAn-3,14-hydroxy DPAn-3,16-hydroxy DPAn-3, and 17-hydroxy DPAn-3; the R and S epimers of the dihydroxy derivatives of DPAn-3, including 7,17-dihydroxy DPAn-3, 10,17-dihydroxy DPAn-3, 8,14-dihydroxy DPAn-3, 16,17-dihydroxy DPAn-3, 13,20-dihydroxy DPAn-3, and 10,20-dihydroxy DPAn-3; and tri-hydroxy derivatives of DPAn-3, including R and S epimers of 7,16,17-trihydroxy DPAn-3. Structures of the DPAn-3 oxylipins are described and/or shown in U.S. Patent Publication No. 2006/0241088, supra.

c) DTAn-6-Derived Oxylipins

DTAn-6-derived oxylipins (also referred to as oxylipins, or more particularly, docosanoids, from DTAn-6) include but are not limited to, any R- or S-epimer of any monohydroxy, dihydroxy, trihydroxy, or multi-hydroxy derivative of DTAn-6, and can include hydroxy derivatizations at any carbon that forms a carbon-carbon double bond in DTAn-6. Some exemplary, novel DTAn-6 derived oxylipins of the present invention include, but are not limited to: the R- and S-epimers of the monohydroxy products of DTAn-6, including 7-hydroxy DTAn-6,10-hydroxy DTAn-6,13-hydroxy DTAn-6, and 17-hydroxy DTAn-6; the R and S epimers of the dihydroxy derivatives of DTAn-6, including 7,17-dihydroxy DTAn-6, 10,17-dihydroxy DTAn-6, and 16,17-dihydroxy DTAn-6; and tri-hydroxy derivatives of DTAn-6, including R and S epimers of 7,16,17-trihydroxy DTAn-6. Structures of the DTAn-6 oxylipins are described and/or shown in U.S. Patent Publication No. 2006/0241088, supra.

d) Other C22-PUFA-Derived Oxylipins

Other novel C22-PUFA-derived oxylipins (also referred to as oxylipins, or more particularly, docosanoids, from a C22-PUFA) include but are not limited to, any R- or S-epimer of any monohydroxy, dihydroxy, trihydroxy, or multi-hydroxy derivative of C22-PUFAs, and can include hydroxy derivatizations at any carbon that forms a carbon-carbon double bond in the C22-PUFAs. Some exemplary, novel docosanoids that are encompassed by the present invention include, but are not limited to 4,5-epoxy-17-hydroxy DPA, 7,8-epoxy DHA, 10,11-epoxy DHA, 13,14-epoxy DHA, 19,20-epoxy DHA, 13,14-dihydroxy DHA, 16,17-dihydroxy DTAn-6,7,16,17-trihydroxy DTAn-6,4,5,17-trihydroxy DTAn-6, 7,16,17-trihydroxy DTAn-3, 16,17-dihydroxy DTAn-3, 16,17-dihydroxy DTRAn-6, 7,16,17-trihydroxy DTRAn-6, 4,5-dihydroxy DTAn-6, and 10,16,17-trihydroxy DTRAn-6.

Structures of these C22-PUFA-derived docosanoids are shown in U.S. Patent Publication No. 2006/0241088, supra.

SDA- and GLA-Derived Oxylipins

Oxylipins particularly useful in the present invention can be derived from SDA or GLA. Such oxylipins include, but are not limited to, any R- or S-epimer of any monohydroxy, dihydroxy or trihydroxy derivative of SDA or GLA, and can include derivatizations at any carbon that forms a carbon-carbon double bond in the reference LCPUFA. SDA- or GLA-derived oxylipins of the present invention also include any product of an enzyme reaction that uses SDA or GLA as a substrate and that is catalyzed by an oxylipin-generating enzyme including, but not limited to lipoxygenases, cyclooxygenases, cytochrome P450 enzymes and other heme-containing enzymes, such as those described in Table 1 (see below). Table 1 provides sufficient information to identify the listed known enzymes, including official names, official symbols, aliases, organisms, and/or sequence database accession numbers for the enzymes.

TABLE 1

Lipoxygenase (LOX), cyclooxygenase (COX), cytochrome P450 (CYP) enzymes and other heme-containing enzymes that can be used to process LCPUFA oils and fatty acids to produce their hydroxyl fatty acid derivatives by methods described herein.

LIPOXYGENASE TYPE ENZYMES

ALOX12
Official Symbol: ALOX12 and Name: arachidonate 12-lipoxygenase [*Homo sapiens*]
Other Aliases: HGNC: 429, LOG12
Other Designations: 12(S)-lipoxygenase; platelet-type 12-lipoxygenase/arachidonate 12-lipoxygenase
Chromosome: 17; Location: 17p13.1GeneID: 239
Alox5
Official Symbol: Alox5 and Name: arachidonate 5-lipoxygenase [*Rattus norvegicus*]
Other Aliases: RGD: 2096, LOX5A
Other Designations: 5-Lipoxygenase; 5-lipoxygenase
Chromosome: 4; Location: 4q42GeneID: 25290
ALOXE3
Official Symbol: ALOXE3 and Name: arachidonate lipoxygenase 3 [*Homo sapiens*]
Other Aliases: HGNC: 13743
Other Designations: epidermal lipoxygenase; lipoxygenase-3
Chromosome: 17; Location: 17p13.1GeneID: 59344
LOC425997
similar to arachidonate lipoxygenase 3; epidermal lipoxygenase; lipoxygenase-3 [*Gallus gallus*]
Chromosome: UnGeneID: 425997
LOC489486
similar to Arachidonate 12-lipoxygenase, 12R type (Epidermis-type lipoxygenase 12) (12R-lipoxygenase) (12R-LOX) [*Canis familiaris*]
Chromosome: 5GeneID: 489486
LOC584973
similar to Arachidonate 12-lipoxygenase, 12R type (Epidermis-type lipoxygenase 12) (12R-lipoxygenase) (12R-LOX) [*Strongylocentrotus purpuratus*]
Chromosome: UnGeneID: 584973
LOC583202
similar to Arachidonate 12-lipoxygenase, 12R type (Epidermis-type lipoxygenase 12) (12R-lipoxygenase) (12R-LOX) [*Strongylocentrotus purpuratus*]
Chromosome: UnGeneID: 583202
LOC579368
similar to Arachidonate 12-lipoxygenase, 12R type (Epidermis-type lipoxygenase 12) (12R-lipoxygenase) (12R-LOX) [*Strongylocentrotus purpuratus*]
Chromosome: UnGeneID: 579368
LOC504803
similar to Arachidonate 12-lipoxygenase, 12R type (Epidermis-type lipoxygenase 12) (12R-lipoxygenase) (12R-LOX) [*Bos taurus*]
Chromosome: UnGeneID: 504803
ALOX5
Official Symbol: ALOX5 and Name: arachidonate 5-lipoxygenase [*Homo sapiens*]Other Aliases: HGNC: 435, 5-LO, 5LPG, LOG5Other Designations: arachidonic acid 5-lipoxygenase; leukotriene A4 synthaseChromosome: 10; Location: 10q11.2GeneID: 240
OSJNBa0057G07.
15 lipoxygenase L-2; lipoxygenase [*Oryza sativa (japonica* cultivar-group)]GeneID: 3044798
Alox15b
Official Symbol: Alox15b and Name: arachidonate 15-lipoxygenase, second type [*Mus musculus*]
Other Aliases: MGI: 1098228, 8-LOX, 8S-LOX, Alox8
Other Designations: 85-lipoxygenase
Chromosome: 11; Location: 11 B4GeneID: 11688
ALOX5AP
Official Symbol: ALOX5AP and Name: arachidonate 5-lipoxygenase-activating protein [*Homo sapiens*]
Other Aliases: HGNC: 436, FLAP
Other Designations: MK-886-binding protein; five-lipoxygenase activating protein TABLE 1-continued Lipoxygenase (LOX), cyclooxygenase (COX), cytochrome P450 (CYP)
enzymes and other heme-containing enzymes that can be used to process LCPUFA
oils and fatty acids to produce their hydroxyl fatty acid derivatives by methods
described herein.

Chromosome: 13; Location: 13q12GeneID: 241
LOC489485
similar to Arachidonate 15-lipoxygenase, type II (15-LOX-2) (8S-lipoxygenase) (8S-LOX) [*Canis familiaris*]
Chromosome: 5GeneID: 489485
LOC557523
similar to Arachidonate 5-lipoxygenase (5-lipoxygenase) (5-LO) [*Danio rerio*]
Chromosome: 15GeneID: 557523
Alox5ap
Official Symbol: Alox5ap and Name: arachidonate 5-lipoxygenase activating protein [*Mus musculus*]
Other Aliases: MGI: 107505, Flap
Other Designations: arachidonate 5 lipoxygenase activating protein
Chromosome: 5GeneID: 11690
LOC562561
similar to Arachidonate 5-lipoxygenase (5-lipoxygenase) (5-LO) [*Danio rerio*]
Chromosome: UnGeneID: 562561
LOC423769
similar to Arachidonate 5-lipoxygenase (5-lipoxygenase) (5-LO) [*Gallus gallus*]
Chromosome: 6GeneID: 423769
LOC573013
similar to Arachidonate 5-lipoxygenase (5-lipoxygenase) (5-LO) [*Danio rerio*]
Chromosome: UnGeneID: 573013
LOC584481
similar to Arachidonate 5-lipoxygenase (5-lipoxygenase) (5-LO)
[*Strongylocentrotus purpuratus*]
Chromosome: UnGeneID: 584481
5LOX-potato
AAD04258. Reports 5-lipoxygenase [S . . . [gi: 2789652]
15-LOX Soybean
P08170. Reports Seed lipoxygenase . . . [gi: 126398]
12-LOX-porcine
D10621. Reports *Sus scrofa* gene f . . . [gi: 60391233]
B) CYCLOOXYGENASE ENZYMES COX2-human
AAN87129. Reports prostaglandin syn . . . [gi: 27151898]
C) HEMOGLOBIN CONTAINING ENZYMES HBA1
Official Symbol: HBA1 and Name: hemoglobin, alpha 1 [*Homo sapiens*]
Other Aliases: HGNC: 4823, CD31
Other Designations: alpha 1 globin; alpha one globin; alpha-1 globin; alpha-1-globin; alpha-2 globin;
alpha-2-globin; hemoglobin alpha 1 globin chain; hemoglobin alpha 2; hemoglobin alpha-1 chain;
hemoglobin alpha-2
Chromosome: 16; Location: 16p13.3GeneID: 3039
HBB
Official Symbol: HBB and Name: hemoglobin, beta [*Homo sapiens*]
Other Aliases: HGNC: 4827, CD113t-C, HBD, hemoglobin
Other Designations: beta globin; beta globin chain; haemoglobin A beta chain; hemoglobin beta
chain; hemoglobin delta Etolia variant
Chromosome: 11; Location: 11p15.5GeneID: 3043
HBG1
Official Symbol: HBG1 and Name: hemoglobin, gamma A [*Homo sapiens*]
Other Aliases: HGNC: 4831, HBGA, HBGR, HSGGL1, PRO2979
Other Designations: A-gamma globin; gamma A hemoglobin; gamma globin; hemoglobin gamma-a
chain; hemoglobin, gamma, regulator of
Chromosome: 11; Location: 11p15.5GeneID: 3047
D) CYTOCHROME P450 TYPE ENZYMES (Gene, Organism, Gene Database: SwissProt, Gene database: EMBL/Genbank/DDBJ)
CYP4A11, *Homo sapiens*, CP4AB HUMAN, L04751 D26481 S67580 S67581 AF525488 AY369778
X71480
CYP4A4, *Oryctolagus cuniculus*, CP4A4 RABIT, L04758 J02818
CYP4A5, *Oryctolagus cuniculus*, CP4A5 RABIT, M28655 X57209
CYP4A6, *Oryctolagus cuniculus*, CP4A6 RABIT, M28656 M29531
CYP4A7, *Oryctolagus cuniculus*, CP4A7 RABIT, M28657 M29530
CYP4B1, *Homo sapiens*, CP4B1 HUMAN, J02871 X16699 AF491285 AY064485 AY064486
CYP4B1, *Oryctolagus cuniculus*, CP4B1 RABIT, M29852 AF176914 AF332576
CYP4C1, *Blaberus discoidalis*, CP4C1 BLADI, M63798
CYP4C21, *Blattella germanica*, CP4CU BLAGE, AF275641

TABLE 1-continued

Lipoxygenase (LOX), cyclooxygenase (COX), cytochrome P450 (CYP)
enzymes and other heme-containing enzymes that can be used to process LCPUFA
oils and fatty acids to produce their hydroxyl fatty acid derivatives by methods
described herein.

CYP4E4, *Drosophila melanogaster*, C4AE1 DROME, AE003423 AL009194 AY058450 U34331
CYP4F11, *Homo sapiens*, CP4FB HUMAN, AF236085 BC016853 AC005336
CYP4F12, *Homo sapiens*, CP4FC HUMAN, AY008841 AB035130 AB035131 AY358977
CYP4F2, *Homo sapiens*, CP4F2 HUMAN, D26480 U02388 AB015306 AF467894 AC005336
BC067437 BC067439 BC067440 AF221943
CYP4F3 *Homo sapiens* CP4F3 HUMAN, D12620 D12621 AB002454 AB002461 AF054821
AY792513
CYP4F8 *Homo sapiens* CP4F8 HUMAN, AF133298
CYP4V2 *Homo sapiens* CP4V2 HUMAN, AY422002 AK122600 AK126473 BC060857
CYP4V2, *Pongo pygmaeus* CP4V2 PONPY, CR858234
CYP4X1, *Homo sapiens* CP4X1 HUMAN, AY358537 AK098065 BC028102
CYP4Z1, *Homo sapiens* CP4Z1 HUMAN, AY262056 AY358631
Cyp4a1, *Rattus norvegicus* CP4A1 RAT, M14972 X07259 M57718
Cyp4a2, *Rattus norvegicus* CP4A2 RAT, M57719 BC078684
Cyp4a3, *Rattus norvegicus* CP4A3 RAT, M33936
Cyp4a8, *Rattus norvegicus* CP4A8 RAT, M37828
Cyp4aa1, *Drosophila melanogaster*, C4AA1 DROME AE003808
Cyp4ac1, *Drosophila melanogaster*, C4AC1 DROME AE003609 AY051602
Cyp4ac2, *Drosophila melanogaster*, C4AC2 DROME, AE003609
Cyp4ac3, *Drosophila melanogaster*, C4AC3 DROME, AE003609 AY061002
Cyp4ad1, *Drosophila melanogaster*, C4AD1 DROME, AE003837 AY061058
Cyp4b1, *Mus musculus*, CP4B1 MOUSE, D50834 BC008996
Cyp4b1 *Rattus norvegicus* CP4B1 RAT, M29853 BC074012
Cyp4c3, *Drosophila melanogaster*, CP4C3 DROME, AE003775 BT010108 U34323
Cyp4d1, *Drosophila melanogaster*, CP4D1 DROME, X67645 AF016992 AF016993 AF016994
AF016995 AF016996 AF016997 AF016998 AF016999 AF017000 AF017001 AF017002 AF017003
AF017004 AE003423 AE003423 Z98269
Cyp4d1, *Drosophila simulans*, CP4D1 DROSI, AF017005
Cyp4d10, *Drosophila mettleri*, C4D10 DROMT, U91634
Cyp4d14, *Drosophila melanogaster*, C4D14 DROME, AE003423 AL009194
Cyp4d2, *Drosophila melanogaster*, CP4D2 DROME, X75955 Z23005 AE003423 AL009194
AY118763 AF017006 AF017007 AF017008 AF017009 AF017010 AF017011 AF017012 AF017013
AF017014 AF017015 AF017016 AF017017 AF017018 -Cyp4d20, *Drosophila melanogaster*,
C4D20 DROME, AE003475
Cyp4d21, *Drosophila melanogaster*, C4D21 DROME, AE003618
Cyp4d8, *Drosophila melanogaster*, CP4D8 DROME, AE003558 AY058442 U34329
Cyp4e1, *Drosophila melanogaster*, CP4E1 DROME, AE003837 AY118793
Cyp4e2, *Drosophila melanogaster*, CP4E2 DROME, U56957 AE003837 AY058518 X86076 U34332
Cyp4e3, *Drosophila melanogaster*, CP4E3 DROME, AE003626 U34330
Cyp4e5, *Drosophila mettleri*, CP4E5 DROMT, U78486
Cyp4f1, *Rattus norvegicus*, CP4F1 RAT, M94548 AF200361
Cyp4f14, *Mus musculus*, CP4FE MOUSE, AB037541 AB037540 AF233644 AK005007 AK018676
BC011228
Cyp4f4, *Rattus norvegicus*, CP4F4 RAT, U39206
Cyp4f5, *Rattus norvegicus*, CP4F5 RAT, U39207
Cyp4f6, *Rattus norvegicus*, CP4F6 RAT, U39208
Cyp4g1, *Drosophila melanogaster*, CP4G1 DROME, AE003417 AL009188 U34328
Cyp4g15, *Drosophila melanogaster*, C4G15 DROME, AF159624 AE003486 AY060719
Cyp4p1, *Drosophila melanogaster*, CP4P1 DROME, AE003834 AY071584 U34327
Cyp4p2, *Drosophila melanogaster*, CP4P2 DROME, AE003834 AY051564
Cyp4p3, *Drosophila melanogaster*, CP4P3 DROME, AE003834 AY075201
Cyp4s3, *Drosophila melanogaster*, CP4S3 DROME AE003498
Cyp4v3, *Mus musculus*, CP4V3 MOUSE, AB056457 AK004724
Cyp4x1, *Rattus norvegicus*, CP4X1 RAT, AF439343
CYP2 Family of Cytochrome P450 Enzymes (sequences from Genbank)

CYP2J2 sequences from GenBank
NM_000775
*Homo sapiens* cytochrome P450, family 2, subfamily J, polypeptide 2 (CYP2J2)
gi|18491007|ref|NM_000775.2|[18491007]
NM_000770
*Homo sapiens* cytochrome P450, family 2, subfamily C, polypeptide 8 (CYP2C8), transcript variant
Hp1-1, mRNA
gi|13787188|ref|NM_000770.2|[13787188]
NM_030878
*Homo sapiens* cytochrome P450, family 2, subfamily C, polypeptide 8 (CYP2C8), transcript variant
Hp1-2, mRNA
gi|13787186|ref|NM_030878.1|[13787186]
NM_023025
*Rattus norvegicus* cytochrome P450, family 2, subfamily J, polypeptide 4 (Cyp2j4), mRNA
gi|61889087|ref|NM_023025.2|[61889087]

TABLE 1-continued

Lipoxygenase (LOX), cyclooxygenase (COX), cytochrome P450 (CYP)
enzymes and other heme-containing enzymes that can be used to process LCPUFA
oils and fatty acids to produce their hydroxyl fatty acid derivatives by methods
described herein.

DN992115
TC119679 Human adult whole brain, large insert, pCMV expression library *Homo sapiens* cDNA
clone TC119679 5' similar to *Homo sapiens* cytochrome P450, family 2, subfamily J, polypeptide 2
(CYP2J2), mRNA sequence
gi|66251946|gb|DN992115.1|[66251946]
Z84061
SSZ84061 Porcine small intestine cDNA library *Sus scrofa* cDNA clone c13d09 5'
similar to cytochrome P450 monooxygenase CYP2J, mRNA sequence
gi|1806390|emb|Z84061.1|[1806390]
BC091149
*Rattus norvegicus* cytochrome P450, family 2, subfamily J, polypeptide 4, mRNA (cDNA clone
MGC: 108684 IMAGE: 7323516), complete cds
gi|60688166|gb|BC091149.1|[60688166]
NW_380169
*Bos taurus* chromosome Un genomic contig, whole genome shotgun sequence
gi|61630302|ref|NW_380169.1|BtUn_WGA215002_1[61630302]
BC032594
*Homo sapiens* cytochrome P450, family 2, subfamily J, polypeptide 2, mRNA (cDNA clone
MGC: 44831 IMAGE: 5527808), complete cds
gi|21595666|gb|BC032594.1|[21595666]
NT_086582
*Homo sapiens* chromosome 1 genomic contig, alternate assembly
gi|51460368|ref|NT_086582.1|Hs1_86277[51460368]
NT_032977
*Homo sapiens* chromosome 1 genomic contig
gi|51458674|ref|NT_032977.7|Hs1_33153[51458674]
CO581852
ILLUMIGEN_MCQ_46633 Katze_MMJJ *Macaca mulatta* cDNA clone IBIUW: 17960 5' similar to
Bases 384 to 953 highly similar to human CYP2J2 (Hs.152096), mRNA sequence
gi|50413382|gb|CO581852.1|[50413382]
AY410198
*Mus musculus* CYP2J2 gene, VIRTUAL TRANSCRIPT, partial sequence, genomic survey sequence
gi|39766166|gb|AY410198.1|[39766166]
AY410197
*Pan troglodytes* CYP2J2 gene, VIRTUAL TRANSCRIPT, partial sequence, genomic survey
sequence
gi|39766165|gb|AY410197.1|[39766165]
AY410196
*Homo sapiens* CYP2J2 gene, VIRTUAL TRANSCRIPT, partial sequence, genomic survey sequence
gi|39766164|gb|AY410196.1|[39766164]
AY426985
*Homo sapiens* cytochrome P450, family 2, subfamily J, polypeptide 2 (CYP2J2) gene, complete cds
gi|37574503|gb|AY426985.1|[37574503]
AB080265
*Homo sapiens* CYP2J2 mRNA for cytochrome P450 2J2, complete cds
gi|18874076|dbj|AB080265.1|[18874076]
AF272142
*Homo sapiens* cytochrome P450 (CYP2J2) gene, complete cds
gi|21262185|gb|AF272142.1|[21262185]
U37143
*Homo sapiens* cytochrome P450 monooxygenase CYP2J2 mRNA, complete cds
gi|18254512|gb|U37143.2|HSU37143[18254512]
AF039089
*Homo sapiens* cytochrome P450 (CYP2J2) gene, partial cds
gi|14486567|gb|AF039089.1|AF039089[14486567]
CYP5 Family of Cytochrome P450 Enzymes (sequences from Genbank)

NM_011539
*Mus musculus* thromboxane A synthase 1, platelet (Tbxas1), mRNA
gi|31981465|ref|NM_011539.2|[31981465]
NM_030984
*Homo sapiens* thromboxane A synthase 1 (platelet, cytochrome P450, family 5, subfamily A)
(TBXAS1), transcript variant TXS-II, mRNA
gi|13699839|ref|NM_030984.1|[13699839]
NM_001061
*Homo sapiens* thromboxane A synthase 1 (platelet, cytochrome P450, family 5, subfamily A)
(TBXAS1), transcript variant TXS-I, mRNA
gi|13699838|ref|NM_001061.2|[13699838]
BC041157
*Homo sapiens* thromboxane A synthase 1 (platelet, cytochrome P450, family 5, subfamily A),
transcript variant TXS-I, mRNA (cDNA clone MGC: 48726 IMAGE: 5755195), complete cds
gi|27371225|gb|BC041157.1|[27371225]

TABLE 1-continued

Lipoxygenase (LOX), cyclooxygenase (COX), cytochrome P450 (CYP)
enzymes and other heme-containing enzymes that can be used to process LCPUFA
oils and fatty acids to produce their hydroxyl fatty acid derivatives by methods
described herein.

CYP8 Family of Cytochrome P450 Enzymes (sequences from Genbank)

NM_000961
*Homo sapiens* prostaglandin I2 (prostacyclin) synthase (PTGIS), mRNA
gi|61676177|ref|NM_000961.3|[61676177]
NM_008968
*Mus musculus* prostaglandin I2 (prostacyclin) synthase (Ptgis), mRNA
gi|31982083|ref|NM_008968.2|[31982083]
D83402
*Homo sapiens* PTGIS(CYP8) gene for prostacyclin synthase, complete cds
gi|60683846|dbj|D83402.2|[60683846]
BC062151
*Mus musculus* prostaglandin I2 (prostacyclin) synthase, mRNA (cDNA clone MGC: 70035
IMAGE: 6512164), complete cds
gi|38328177|gb|BC062151.1|[38328177]

(a) SDA-derived Oxylipins

SDA-derived oxylipins (also referred to as oxylipins from SDA) include, but are not limited to, any R- or S-epimer of any monohydroxy, dihydroxy, or trihydroxy derivative of SDA, and can include hydroxy derivatizations at any carbon that forms a carbon-carbon double bond in SDA. Some exemplary, novel SDA-derived oxylipins of the present invention include, but are not limited to: the R- and S-epimers of the monohydroxy products of SDA, including 6-hydroxy SDA, 7-hydroxy SDA, 10-hydroxy SDA, 12-hydroxy SDA, 15-hydroxy SDA and 16-hydroxy SDA; the R and S epimers of dihydroxy derivatives of SDA, including 6,13-dihydroxy SDA and 6,16 dihydroxy SDA, as well as dihydroxy derivatives with hydroxyl groups at any two carbons at the C6, C7, C9, C10, C12, C13, C15 or C16 positions of SDA; and the R and S epimers of trihydroxy derivatives of SDA, including trihydroxy derivatives with hydroxyl groups at any three of the carbons at the C6, C7, C9, C10, C12, C13, C15 or C16 positions of SDA. 9-hydroxy SDA and 13-hydroxy SDA represent previously described oxylipins of SDA, but the novel use of such oxylipin in the regulation of inflammation and neurodegeneration or in other nutritional, therapeutic or other (e.g., cosmetic, aquaculture) applications described herein, as well as the enrichment of such oxylipin in oils as described herein is encompassed by the present invention. Structures of the SDA oxylipins are described and/or shown in Example 1 and FIGS. 1 and 3.

(b) GLA-Derived Oxylipins

GLA-derived oxylipins (also referred to as oxylipins from GLA) include, but are not limited to, any R- or S-epimer of any monohydroxy, dihydroxy or trihydroxy derivative of GLA, and can include hydroxy derivatizations at any carbon that forms a carbon-carbon double bond in GLA. Some exemplary, novel GLA derived oxylipins of the present invention include, but are not limited to: the R- and S-epimers of the monohydroxy products of GLA, including 7-hydroxy GLA and 12-hydroxy GLA; the R and S epimers of dihydroxy derivatives of GLA, including 6,13-dihydroxy GLA; and the R and S epimers of trihydroxy derivatives of GLA. 6-hydroxy GLA, 9-hydroxy GLA, 10-hydroxy GLA and 13-hydroxy GLA represent previously described oxylipins of GLA, but the novel use of such oxylipins in the regulation of inflammation and neurodegeneration or in other nutritional, therapeutic or other (e.g., cosmetic, aquaculture) applications described herein, as well as the enrichment of such oxylipin in oils as described herein is encompassed by the present invention. Structures of the GLA oxylipins are described and/or shown in Example 2 and FIGS. 2 and 4.

SDA- and GLA-derived oxylipins, as well as analogs or derivatives of any of such oxylipins of the present invention, can be produced by chemical synthesis or biological synthesis, including by de novo synthesis or enzymatic conversion of a substrate. Alternatively, such oxylipins can be produced by isolation, enrichment and/or conversion of substrates from natural sources (described below). According to the present invention, reference to an oxylipin "derived from" a specific LCPUFA, such as an "SDA-derived oxylipin" or an "SDA oxylipin derivative", or an "SDA oxylipin analog", by way of example (i.e., this discussion applies equivalently to oxylipins from GLA), refers to an oxylipin that has been produced by any method, using the knowledge of the structure of an oxylipin that can be produced using SDA as a substrate. Such an oxylipin need not be produced by an enzymatic reaction or biological system, but, as mentioned above, can alternatively be chemically synthesized de novo. In addition, analogs or derivatives of naturally occurring SDA oxylipins may be designed based on the structure of the naturally occurring SDA oxylipins, but which differ from the naturally occurring SDA oxylipin by at least one modification. Such analogs may also be synthesized de novo using chemical synthesis methods or by using modifications of biological production methods (e.g., enzyme reactions). Methods of producing oxylipins according to the present invention, including methods of enriching natural sources of such oxylipins, and by enzymatic conversion of substrates are described herein. Chemical synthesis methods for compounds such as oxylipins are also known in the art and can readily be applied to the novel oxylipin compounds of the present invention. Such methods are also described herein.

According to the present invention, the language "SDA- or GLA-oxylipin-like compounds" or "SDA- or GLA-oxylipin analogs" or "SDA- or GLA-oxylipin derivatives" is intended to include analogs of any oxylipins described herein. Similar language can also be used to more generally describe analogs and derivatives of any oxylipins as described herein (e.g., oxylipin-like compounds, oxylipin analogs, oxylipin derivatives).

As used herein, the term "analog" refers to a chemical compound that is structurally similar to another compound but differs slightly in composition (as in the replacement of one atom by an atom of a different element or in the presence of a particular functional group, or the replacement of one functional group by another functional group). Thus, an analog is a compound that is similar or comparable in function and appearance, but not in structure or origin to the reference compound. For example, the reference compound can be a reference oxylipin such as any oxylipin derived from SDA or GLA, and an analog is a substance possessing a chemical structure or chemical properties similar to those of the reference docosanoid.

The terms "substituted", "substituted derivative" and "derivative", when used to describe a compound of the present invention, means that at least one hydrogen bound to the unsubstituted compound is replaced with a different atom or a chemical moiety. Examples of substituents include, but are not limited to, hydroxy, alkyl, halogen, nitro, cyano, heterocycle, aryl, heteroaryl, amino, amide, ester, ether, carboxylic acid, thiol, thioester, thioether, sulfoxide, sulfone, carbamate, peptidyl, $PO_3H_2$, and mixtures thereof.

Although a derivative has a similar physical structure to the parent compound, the derivative may have different chemical and/or biological properties than the parent compound. Such properties can include, but are not limited to, increased or decreased activity of the parent compound, new activity as compared to the parent compound, enhanced or decreased bioavailability, enhanced or decreased efficacy, enhanced or decreased stability in vitro and/or in vivo, and/or enhanced or decreased absorption properties.

It will be appreciated by those skilled in the art that compounds of the invention having a chiral center may exist in and be isolated in optically active and racemic forms. Some compounds may exhibit polymorphism. It is to be understood that the present invention encompasses any racemic, optically-active, polymorphic, or stereoisomeric form, or mixtures thereof, of a compound of the invention, which possess the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase) and how to determine anti-inflammatory activity, for example, using standard tests described herein, or using other similar tests which are well known in the art. Accordingly, the present invention includes any R-epimer, S-epimer, and any compound having two asymmetric centers, including, but not limited to, R/S epimers, S/R epimers, R/R epimers and S/S epimers. General reference to an R-epimer or S-epimer is intended to cover all combinations of asymmetric and symmetric chiral centers.

Prodrugs of any of the oxylipins described herein, and particularly, any specific oxylipins as shown, for example, in FIGS. 1-4, may be identified using routine techniques known in the art. Various forms of prodrugs are known in the art. For examples of such prodrug derivatives, see, for example, a) Design of Prodrugs, edited by H. Bundgaard, (Elsevier, 1985) and Methods in Enzymology, Vol. 42, p. 309-396, edited by K. Widder, et al. (Academic Press, 1985); b) A Textbook of Drug Design and Development, edited by Krogsgaard-Larsen and H. Bundgaard, Chapter 5 "Design and Application of Prodrugs," by H. Bundgaard p. 113-191 (1991); c) H. Bundgaard, Advanced Drug Delivery Reviews, 8, 1-38 (1992); d) H. Bundgaard, et al., Journal of Pharmaceutical Sciences, 77:285 (1988); and e) N. Kakeya, et al., Chem. Pharm. Bull., 32: 692 (1984), each of which is specifically incorporated herein by reference.

In addition, the invention also includes solvates, metabolites, and salts (preferably pharmaceutically acceptable salts) of compounds of any of the oxylipins described herein, and particularly, any specific oxylipins as shown, for example, in FIGS. 1-4.

The term "solvate" refers to an aggregate of a molecule with one or more solvent molecules. A "metabolite" is a pharmacologically active product produced through in vivo metabolism in the body or organism of a specified compound or salt thereof. Such products may result for example from the oxidation, reduction, hydrolysis, amidation, deamidation, esterification, deesterification, enzymatic cleavage, and the like, of the administered or produced compound. Accordingly, the invention includes metabolites of compounds of any of the oxylipins described herein, and particularly, any specific oxylipins as shown, for example, in FIGS. 1-4, including compounds produced by a process comprising contacting a compound of this invention with an organism for a period of time sufficient to yield a metabolic product thereof.

A "pharmaceutically acceptable salt" or "salt" as used herein, includes salts that retain the biological effectiveness of the free acids and bases of the specified compound and that are not biologically or otherwise undesirable. A compound of the invention may possess a sufficiently acidic, a sufficiently basic, or both functional groups, and accordingly react with any of a number of inorganic or organic bases, and inorganic and organic acids, to form a pharmaceutically acceptable salt. Examples of pharmaceutically acceptable salts include those salts prepared by reaction of the compounds of the present invention with a mineral or organic acid or an inorganic base, such salts including sulfates, pyrosulfates, bisulfates, sulfites, bisulfites, phosphates, monohydrogenphosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyn-1,4-dioates, hexyne-1,6-dioates, benzoates, chlorobenzoates, methylbenzoates, dinitromenzoates, hydroxybenzoates, methoxybenzoates, phthalates, sulfonates, xylenesulfonates, pheylacetates, phenylpropionates, phenylbutyrates, citrates, lactates, gamma.-hydroxybutyrates, glycollates, tartrates, methanesulfonates, propanesulfonates, naphthalene-1-sulfonates, naphthalene-2-sulfonates, and mandelates. Since a single compound of the present invention may include more than one acidic or basic moieties, the compounds of the present invention may include mono, di or tri-salts in a single compound.

If the inventive compound is a base, the desired pharmaceutically acceptable salt may be prepared by any suitable method available in the art, for example, treatment of the free base with an acidic compound, particularly an inorganic acid, such as hydrochloric acid, hydrobromic acid, sulfuric acid, nitric acid, phosphoric acid and the like, or with an organic acid, such as acetic acid, maleic acid, succinic acid, mandelic acid, fumaric acid, malonic acid, pyruvic acid, oxalic acid, glycolic acid, salicylic acid, a pyranosidyl acid, such as glucuronic acid or galacturonic acid, an alphahydroxy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, or the like.

If the inventive compound is an acid, the desired pharmaceutically acceptable salt may be prepared by any suitable method, for example, treatment of the free acid with an inorganic or organic base. Preferred inorganic salts are those formed with alkali and alkaline earth metals such as lithium, sodium, potassium, barium and calcium. Preferred organic base salts include, for example, ammonium, dibenzylammonium, benzylammonium, 2-hydroxyethylammonium, bis(2-hydroxyethyl)ammonium, phenylethylbenzylamine, dibenzylethylenediamine, and the like salts. Other salts of acidic moieties may include, for example, those salts formed with procaine, quinine and N-methylglusoamine, plus salts formed with basic amino acids such as glycine, ornithine, histidine, phenylglycine, lysine and arginine.

Oils, Compositions, Formulations or Products Containing SDA, GLA, Other LCPUFAs and/or Oxylipins Derived Therefrom The present invention includes oils, compositions, formulations and products comprising LCPUFAs and/or LCPUFA oxylipins described herein. According to the present invention, the term "product" can be used to generally or generically describe any oil, composition, or formulation of the present invention, although one term might be preferred over another depending on the context of use of the product. In one embodiment of the invention, oils, compositions, and formulations include at least SDA, GLA, or oxylipins derived therefrom, or any combinations thereof, and may additionally include any other LCPUFAs and/or any oxylipins derived therefrom. Such oxylipins can be produced by any chemical or biological (biogenic) method, including de novo synthesis, enzymatic conversion from any source (e.g., by enzymes including lipoxygenases, cyclooxygenases, cytochrome P450 enzymes and other heme-containing enzymes), purification from any source, and production from any biological source (e.g., microbial, plant, animal sources).

In one embodiment of the invention, oils are enriched for the presence of SDA- and/or GLA-derived oxylipins, and may further include enrichment for other LCPUFA-derived oxylipins (also known as an LCPUFA oxylipin), such as oxylipins derived from DHA, EPA, DPAn-6, DTAn-6, and/or DPAn-3. In another embodiment, oils, compositions or formulations containing such SDA-, GLA- or other LCPUFA-derived oxylipins are produced, processed or treated to retain, and/or improve the stability, absorption, bioactivity, bioavailability or efficacy of the LCPUFA oxylipins in the oil, compositions or formulations. Various methods of producing, processing and supplementing oils, compositions or formulations are described below.

Sources of LCPUFAs and LCPUFA-Derived Oxylipins for Use in the Present Invention Any source of LCPUFA (e.g., SDA and/or GLA) can be used to produce the LCPUFAs, oxylipins, oils, compositions or formulations of the present invention, including, for example, animal (invertebrates and vertebrates), plant and microbial sources. Fish oil sources of SDA include herring oil, anchovy oil, pilchard oil, sardine oil, menhaden oil, and the fatty acids from Norway pout, blue whiting, saith (*Pollachius virens*) and Mullers pearlsides (*Maurolicus muelleri*).

Examples of animal sources include aquatic animals (e.g., fish, marine mammals, and crustaceans such as krill and other euphausids) and lipids extracted from animal tissues (e.g., brain, liver, eyes, etc.).

Other preferred sources include microorganisms and plants. Preferred microbial sources of LCPUFAs include algae, fungi (including yeast and filamentous fungi of the genus *Mortierella*), protists and bacteria. The use of a microorganism source, such as algae, can provide organoleptic advantages, i.e., fatty acids from a microorganism source may not have the fishy taste and smell that fatty acids from a fish source tend to have. However, fish oils are also included in the present invention. While fish oils may naturally undergo oxidation processes that produce aldehydes and ketones that impart bad odors and tastes to such fish oils, the present invention takes advantage of "directed" or "targeted" oxidation of specific compounds to produce oxylipins or mixtures of oxylipins that provide a beneficial quality to the oils containing such oxylipins, including animal oils (e.g., fish oils) and plant oils, or combinations thereof. In a preferred embodiment, any oils containing GLA and/or SDA, and further comprising DHA, EPA, DPAn-6, DTAn-6 and/or DPAn-3, are utilized in the invention.

In one aspect of the invention, the LCPUFA source comprises algae or protists or fungi. Preferred algal and protist genera are members of the kingdom Stramenopila, and more preferably, are members of the algal groups: dinoflagellates, diatoms, chrysophytes, green algae or cryptomonads. Algal sources of GLA include species of *Scenedesmus* including, but not limited to *S. quadricauda* and *S. obliquus*; and, species of *Ochromonas* including, but not limited to *Ochromonas danica*. Algal sources of SDA include the following: species of *Dunaliella* including, but not limited to *D. primolecta* and *D. tertiolecta*, species of *Heteromastix* including, but not limited to *H. rotunda, Isochrysis galbana, Dicrateria inornata, Gonaulax polyhedra, Amphidinium carteri, Peridinium*, species of the Cryptophyceae including species of the genera *Hemiselmis* including, but not limited to *H. rufescens, H. brunnescens, H. virescens*; species of *Cryptomonas* including, but not limited to *C. appendiculata, C. maculata, C. ovata*; and species of *Rhodomonas* including, but not limited to *Rhodomonas* lens.

More preferably, the LCPUFA source comprises fungal sources of GLA including the following: species of the genus *Choanephora* including, but not limited to *C. curcurbitarum*; species of the genus *Mucor* including, but not limited to *M. pyriforme, M. miehei, M. inaequisporus, M. rouxii, M. circinelloides* (also known as *Mucor javanicus*); species of the genus *Rhizopus*; species of the genus *Mortierella* including, but not limited to *M. ramanniana, M. alpina, M. isabellina, M. hygrophila, M. parvispora*, and *M. elongata*; species of the genus *Cunninghamella* including, but not limited to *Cunninghamella japonica*; species of the genus *Entomophtora* including, but not limited to *E. exitalis*; species of *Conidiobolus* including, but not limited to *C. heterosporus, C. globuliferus, C. humicola*, and *C. undulatus*.

More preferably, the LCPUFA source comprises the oil from oilseed crop sources of SDA and GLA including species of *Echium* including, but not limited to *E. plantagineum* (echium oil); species of the family Boraginaceae including, but not limited to *Borago officinalis* (borage oil), *Anchusa capensis, Lappula echinata, Myosotis arvensis* and *Onosmodium occidentalis* and *Trichodesma lanicum* (trichodesma oil); species of *Cannabis* including, but not limited to *Cannabis sativa* (hemp oil); species of *Oenothffa* including, but not limited to *O. bionnis* (evening primrose oil); species of *Ribes* including, but not limited to *Ribes nigrum* (black current oil).

Sources of other LCPUFAs, such as DHA, EPA, DPAn-6, DPAn-3 and DTAn-6 are known and have been described in detail, for example, in U.S. Patent Publication No. 2006/0241088, supra.

In one aspect, the organism-sources of oils are genetically engineered to enhance the production of LCPUFAs and/or LCPUFA oxylipins, and particularly, SDA and/or GLA and/or SDA-derived oxylipins and/or GLA-derived oxylipins. The more preferred sources are microorganisms (which can be grown in fermentors), or oilseed crops. For example, microorganisms and plants can be genetically engineered to express genes that produce LCPUFAs, and particularly, SDA- or GLA-derived LCPUFAs. For SDA and GLA, such genes typically include genes encoding proteins involved in the classical fatty acid synthase pathways. For longer chain PUFAs (e.g., 20 carbon and higher), such genes typically include genes encoding proteins involved in the classical fatty acid synthase pathways, or genes encoding proteins involved in the PUFA polyketide synthase (PKS) pathway. The genes and proteins involved in the classical fatty acid synthase pathways, and genetically modified organisms, such as plants, transformed with such genes, are described, for example, in Napier and Sayanova, *Proceedings of the Nutrition Society* (2005), 64:387-393; Robert et al., *Functional Plant Biology* (2005) 32:473-479; or U.S. Patent Application Publication 2004/0172682. The PUFA PKS pathway, genes and proteins included in this pathway, and genetically modified microorganisms and plants transformed with such genes for the expression and production of PUFAs are described in detail in: U.S. Pat. No. 6,566,583; U.S. Patent Application Publication No. 20020194641, U.S. Patent Application Publication No. 20040235127A1, and U.S. Patent Application Publication No. 20050100995A1, each of which is incorporated herein by reference in its entirety.

Preferred oilseed crops for genetic modification/engineering include, but are not limited to soybeans, corn, safflower, sunflower, canola, flax, or rapeseed, linseed, and tobacco that have been genetically modified to produce LCPUFAs as described above, and particularly, SDA and/or GLA. More preferably, the oilseed crops also possess, or can be modified to possess (e.g., by genetic engineering), enzyme systems for converting the LCPUFA to its hydroxy derivative forms (i.e., oxylipin). Such enzymes are well known in the art and are described, for example, in Table 1.

Preferred algal or protists or fungal sources for genetic modification or transformation include those listed above and dinoflagellates including members of the genus *Crypthecodinium* and even more preferably, members of the species *Crypthecodinium cohnii*. Additional fungal sources would include any species of oleaginous yeast (yeast which can make more than 20% of their weight as fatty acids. Additional algal candidates would include members of the thraustochytrids. Developments have resulted in frequent revision of the taxonomy of the Thraustochytrids (thraustochytrids). Taxonomic theorists generally place Thraustochytrids with the algae or algae-like protists. However, because of taxonomic uncertainty, it would be best for the purposes of the present invention to consider the strains described in the present invention as Thraustochytrids to include the following organisms: Order: Thraustochytriales; Family: Thraustochytriaceae (Genera: *Thraustochytrium* (which for this application, includes *Ulkenia*, although some consider it to be a separate genus), *Schizochytrium*, *Japonochytrium*, *Aplanochytrium*, or *Elina*) or Labyrinthulaceae (Genera: *Labyrinthula*, *Labyrinthuloides*, or *Labyrinthomyxa*). Also, the following genera are sometimes included in either family Thraustochytriaceae or Labyrinthulaceae: *Althornia*, *Corallochytrium*, *Diplophyrys*, and *Pyrrhosorus*), and for the purposes of this invention are encompassed by reference to a Thraustochytrid or a member of the order Thraustochytriales. It is recognized that at the time of this invention, revision in the taxonomy of Thraustochytrids places the genus *Labyrinthuloides* in the family of Labyrinthulaceae and confirms the placement of the two families Thraustochytriaceae and Labyrinthulaceae within the Stramenopile lineage. It is noted that the Labyrinthulaceae are sometimes commonly called labyrinthulids or labyrinthula, or labyrinthuloides and the Thraustochytriaceae are commonly called thraustochytrids, although, as discussed above, for the purposes of clarity of this invention, reference to Thraustochytrids encompasses any member of the order Thraustochytriales and/or includes members of both Thraustochytriaceae and Labyrinthulaceae. Information regarding such algae can be found, for example, in U.S. Pat. Nos. 5,407,957, 5,130,242 and 5,340,594, which are incorporated herein by reference in their entirety. Other preferred LCPUFA and oxylipin sources and sources for genetic engineering for use in the present invention include microorganisms from a genus including, but not limited to: *Thraustochytrium*, *Japonochytrium*, *Aplanochytrium*, *Elina* and *Schizochytrium* within the Thraustochytriaceae, and *Labyrinthula*, *Labyrinthuloides*, and *Labyrinthomyxa* within the Labyrinthulaceae. Preferred species within these genera include, but are not limited to: any species within *Labyrinthula*, including *Labyrinthula* sp., *Labyrinthula algeriensis*, *Labyrinthula cienkowskii*, *Labyrinthula chattonii*, *Labyrinthula coenocystis*, *Labyrinthula macrocystis*, *Labyrinthula macrocystis atlantica*, *Labyrinthula macrocystis macrocystis*, *Labyrinthula magnifica*, *Labyrinthula minuta*, *Labyrinthula roscoffensis*, *Labyrinthula valkanovii*, *Labyrinthula vitellina*, *Labyrinthula vitellina pacifica*, *Labyrinthula vitellina vitellina*, *Labyrinthula zopfii*; any *Labyrinthuloides* species, including *Labyrinthuloides* sp., *Labyrinthuloides minuta*, *Labyrinthuloides schizochytrops*; any *Labyrinthomyxa* species, including *Labyrinthomyxa* sp., *Labyrinthomyxa pohlia*, *Labyrinthomyxa sauvageaui*, any *Aplanochytrium* species, including *Aplanochytrium* sp. and *Aplanochytrium kerguelensis*; any *Elina* species, including *Elina* sp., *Elina marisalba*, *Elina sinorifica*; any *Japonochytrium* species, including *Japonochytrium* sp., *Japonochytrium marinum*; any *Schizochytrium* species, including *Schizochytrium* sp., *Schizochytrium aggregatum*, *Schizochytrium limacinum*, *Schizochytrium minutum*, *Schizochytrium octosporum*; and any *Thraustochytrium* species, including *Thraustochytrium* sp., *Thraustochytrium aggregatum*, *Thraustochytrium arudimentale*, *Thraustochytrium aureum*, *Thraustochytrium benthicola*, *Thraustochytrium globosum*, *Thraustochytrium kinnei*, *Thraustochytrium motivum*, *Thraustochytrium pachydermum*, *Thraustochytrium proliferum*, *Thraustochytrium roseum*, *Thraustochytrium striatum*, *Ulkenia* sp., *Ulkenia minuta*, *Ulkenia profunda*, *Ulkenia radiate*, *Ulkenia sarkariana*, and *Ulkenia visurgensis*. Particularly preferred species within these genera include, but are not limited to: any *Schizochytrium* species, including *Schizochytrium aggregatum*, *Schizochytrium limacinum*, *Schizochytrium minutum*; or any *Thraustochytrium* species (including former *Ulkenia* species such as *U. visurgensis*, *U. amoeboida*, *U. sarkariana*, *U. profunda*, *U. radiata*, *U. minuta* and *Ulkenia* sp. BP-5601), and including *Thraustochytrium striatum*, *Thraustochytrium aureum*, *Thraustochytrium roseum*; and any *Japonochytrium* species. Particularly preferred strains of Thraustochytriales include, but are not limited to: *Schizochytrium* sp. (S31) (ATCC 20888); *Schizochytrium* sp. (S8) (ATCC 20889); *Schizochytrium* sp. (LC-RM) (ATCC 18915); *Schizochytrium* sp. (SR21); *Schizochytrium aggregatum* (Goldstein et Belsky) (ATCC 28209); *Schizochytrium limacinum* (Honda et Yokochi) (IFO 32693); *Thraustochytrium* sp. (23B) (ATCC 20892); *Thraustochytrium striatum* (Schneider) (ATCC 24473); *Thraustochytrium aureum* (Goldstein) (ATCC 34304); *Thraustochytrium roseum* (Goldstein) (ATCC 28210); *Japonochytrium* sp. (L1) (ATCC 28207); *Thraustochytrium* sp. 12B (ATCC 20890); *Thraustochytrium* sp. U42-2 (ATCC 20891); and *Labyrinthula* (labyrinthulid) strain L59 (Kumon) (IPOD AIST No. FERM P-19897).

Genetic transformation techniques for microorganisms and plants are well-known in the art. It is an embodiment of the present invention that the nucleic acid molecules encoding any one or more enzymes for converting an LCPUFA to its hydroxy-derivative form (and, if required, cofactors therefor) can be used to transform plants or microorganisms to initiate, improve and/or alter (modify, change) the oxylipin production capabilities of such plants or microorganisms. Transformation techniques for microorganisms are well known in the art and are discussed, for example, in Sambrook et al., 1989, *Molecular Cloning: A Laboratory Manual*, Cold Spring Harbor Labs Press. A general technique for transformation of dinoflagellates, which can be adapted for use with *Crypthecodinium cohnii*, is described in detail in Lohuis and Miller, *The Plant Journal* (1998) 13(3): 427-435. A general technique for genetic transformation of Thraustochytrids, for example, is described in detail U.S. Patent Application Publication No. 20030166207, published Sep. 4, 2003.

Methods for the genetic engineering of plants are also well known in the art. For instance, numerous methods for plant transformation have been developed, including biological and physical transformation protocols. See, for example, Miki et al., "Procedures for Introducing Foreign DNA into Plants" in *Methods in Plant Molecular Biology and Biotechnology*, Glick, B. R. and Thompson, J. E. Eds. (CRC Press, Inc., Boca Raton, 1993) pp. 67-88. In addition, vectors and in vitro culture methods for plant cell or tissue transformation and regeneration of plants are available. See, for example, Gruber et al., "Vectors for Plant Transformation" in *Methods in Plant Molecular Biology and Biotechnology*, Glick, B. R. and Thompson, J. E. Eds. (CRC Press, Inc., Boca Raton, 1993) pp. 89-119. See also, Horsch et al., *Science* 227:1229 (1985); Kado, C. I., *Crit. Rev. Plant. Sci.* 10:1 (1991); Moloney et al., *Plant Cell Reports* 8:238 (1989); U.S. Pat. No. 4,940,838; U.S. Pat. No. 5,464,763; Sanford et al., *Part. Sci. Technol.* 5:27 (1987); Sanford, J. C., *Trends Biotech.* 6:299 (1988); Sanford, J. C., *Physiol. Plant* 79:206 (1990); Klein et al., *Biotechnology* 10:268 (1992); Zhang et al., *Bio/Technology* 9:996 (1991); Deshayes et al., *EMBO J.*, 4:2731 (1985); Christou et al., *Proc Natl. Acad. Sci. USA* 84:3962 (1987); Hain et al., *Mol. Gen. Genet.* 199:161 (1985); Draper et al., *Plant Cell Physiol.* 23:451 (1982); Donn et al., In Abstracts of VIth International Congress on Plant Cell and Tissue Culture IAPTC, A2-38, p. 53 (1990); D'Halluin et al., *Plant Cell* 4:1495-1505 (1992) and Spencer et al., *Plant Mol. Biol.* 24:51-61 (1994).

Preferably, microorganisms or oilseed plants useful as sources of LCPUFAs and oxylipins derived therefrom, and particularly, SDA and/or GLA and oxylipins derived therefrom, are microorganisms or plants that produce PUFAs (either naturally or by genetic engineering) having C18 or greater polyunsaturated fatty acids. Preferably, the LCPUFAs produced by the microorganism or plants have 3, 4, or more double bonds, including, but not limited to, SDA (18:4n-3) or GLA (18:3n-6). The microorganisms and plants may also produce C20 or greater LCPUFAs with 4, 5 or more double bonds, including, but not limited to: EPA (20:5n-3), DHA (C22:6n-3), DPAn-3(22:5n-3), DPAn-6(22:5n-6), DTAn-6 (22:4n-6) or combinations of these LCPUFAs.

In another embodiment, it is preferred that the microorganism or plant sources of LCPUFAs naturally express enzymes such as cyclooxygenases, lipoxygenases, cytochrome P450 enzymes (including hydroxylases, peroxidases, and oxygenases), and/or other heme-containing enzymes for biochemical conversion of LCPUFAs to oxylipins (e.g., to the hydroxy, peroxide, or epoxide derivatives of LCPUFAs). The invention also includes organisms (e.g., plants or microorganisms) that have been naturally selected or genetically engineered to express these enzymes and/or to have enhanced activity of these enzymes in the organism. Organisms can be genetically engineered to express or target any enzyme that catalyzes the biochemical conversion of LCPUFAs to oxylipins such as cyclooxygenases, lipoxygenases, cytochrome P450 enzymes (including hydroxylases, peroxidases, and oxygenases), and/or other heme-containing enzymes for biochemical conversion of LCPUFAs to oxylipins.

Numerous examples of such enzymes are known in the art and are listed in Table 1, although the invention is not limited to these particular enzymes. The enzymes in Table 1 are described by their name, official symbols, aliases, organisms, and/or by reference to the database accession number in the National Center for Biotechnology Information that contains the sequence information for the enzymes and genes encoding such enzymes. All of the information included in each of the database accession numbers is incorporated herein by reference. These enzymes and the genes encoding such enzymes, or homologues (including natural variants) thereof, can be used to genetically engineer an organism that produces LCPUFAs (e.g., SDA and/or GLA) to express the enzyme or to target an endogenous form of the enzyme to initiate, increase or enhance the activity of the enzyme in the organism. Optionally, these enzymes can be targeted to a particular compartment (e.g., plastids in plants), which is separated from compartments containing LCPUFAs, regulating the potential for formation and degradation of oxylipins produced in vivo. The enzymes (endogenous or recombinant) may be placed under the control of an inducible promoter, so that the production of oxylipins from LCPUFAs, including SDA and GLA, can be controlled in the organism. For example, in a plant, oxylipins can be formed during post-harvest processing in which the oilseeds are disrupted to allow contact of the LCPUFAs such as SDA or GLA with oxygenase enzymes.

Microbial or plant cell sources of LCPUFAs useful in the present invention preferably include those microorganisms or plant cells that can be grown in a fermentor or photobioreactor. More preferably, microbial or plant cell sources of LCPU-FAs useful in the present invention preferably include those microorganisms or plant cells that can be grown heterotrophically in fermentors.

Unique Characteristics of Oils Produced by the Present Invention

Oils containing oxylipins of LCPUFAs described herein have unique characteristics as compared to oxylipins that are chemically synthesized or produced by enzymatic conversion in vitro as described prior to the present invention. The LCPUFA oxylipins, and particularly the oxylipins derived from SDA or GLA, are present in the oils in their free and/or esterifed forms. In the esterified form, the LCPUFA oxylipins, and particularly the oxylipins derived from SDA or GLA, can be present in the triglyceride, diglyceride, monoglyceride, phospholipid, sterol ester and/or wax ester forms. The esterified forms of the oxylipins of the present invention also represent novel forms of oxylipins, the presence of which can be enhanced, stabilized or retained in oils or compositions of the present invention. Without being bound by theory, the present inventors believe that once the LCPUFA oxylipins, and in particular, the oxylipins derived from SDA or GLA, are formed in the free fatty acid form, they can be re-esterified into one of the esterifed forms. Alternatively, the fatty acid molecules can be converted to oxylipins while they are still in an esterifed form.

The LCPUFA oil processed by the methods described according to the present invention (see below) will have total LCPUFA oxylipin concentrations, and in particular total SDA- and/or GLA-derived oxylipin concentrations, that are at least 2×, at least 3×, at least 4×, at least 5×, at least 10×, at least 20×, at least 50×, at least 100×, at least 200×, at least 400×, at least 1,000×, or at least 5,000× higher (including any other increment of 1×, e.g., 20×, 21×, 22×, etc.) than the trace concentrations normally found in LCPUFA oils that have been obtained through the standard refining, bleaching, and deodorization process commonly used for edible oils. LCPUFA oils produced by the processes outlined according to the present invention will preferably contain at least 1 µg, at least 5 µg, at least 10 µg, at least 15 µg, at least 20 µg, at least 30 µg, at least 50 µg, at least 100 µg, at least 200 µg, at least 500 µg, at least 1,000 µg, at least 2,000 µg, at least 5,000 µg, at least 10,000 µg, or at least 50,000 µg or more of at least one or more LCPUFA oxylipins, and in particular, SDA- and/or GLA-derived oxylipins, per gram of oil (including any other increment in 0.1 µg increments). It is noted that through processing and purification of oils or compositions, the LCFUA oxylipin concentrations could actually be much higher (e.g., approaching 100%) during the production phase, although the oils and compositions would typically be diluted or titrated to the amounts described above prior to being used in a nutritional, therapeutic, or other process.

The oils produced from the present invention (including mono- di and trihydroxy oxylipin forms), are enriched preferably with hydroxyl forms of SDA and/or GLA, and in a further embodiment, also with hydroxyl forms of DHA and/or EPA and/or DPAn-3 and/or DPAn-6 and/or DTAn-6. LCPUFA hydroxy derivative-rich oils from this invention can be enriched with hydroxy forms of LCPUFA, including derivatives from just one LCPUFA (e.g. from SDA or GLA) or from a combination of LCPUFAs that include derivatives from SDA or GLA (for example, DHA plus SDA or GLA, or DPAn-6 plus SDA or GLA, etc.).

SDA and/or GLA Oils, Compositions and Formulations

One embodiment of the present invention includes the use of the LCPUFAs themselves, and particularly, SDA and/or GLA, as anti-inflammatory or neuroprotective agents (i.e., the LCPUFAs are provided, alone or in combination with oxylipin metabolites thereof). SDA and/or GLA can be provided alone or in combination with other LCPUFAs, and preferably DPAn-6, DPAn-3, DTAn-6, DHA and/or EPA. Preferably, SDA and/or GLA used in the present invention is provided in one of the following forms: as triglyceride containing SDA and/or GLA, as a phospholipid containing SDA and/or GLA, as a free fatty acid, as an ethyl or methyl ester of SDA and/or GLA.

In a preferred embodiment, the SDA and/or GLA is provided in the form of an oil, and preferably a microbial oil (wild-type or genetically modified) or a plant oil from an oil seed plant that has been modified with genes that catalyze the production of LCPUFAs. Preferred microbial and oilseed sources have been described in detail above. Preferably, the SDA and/or GLA to be used in the present invention, including oils or compositions containing such LCPUFAS and/or oxylipin-derivatives thereof, contains one or more of the following additional LCPUFAs or oxylipin-derivatives thereof: DPAn-6, DPAn-3, DTAn-6, DHA or EPA. Most preferably, the additional LCPUFA is DHA or DPAn-6.

Oils, compositions, or formulations (or any products) useful in the present invention preferably comprise SDA and/or GLA in an amount that is at least about 2 weight percent, or at least about 5 weight percent, or at least about 10 weight percent, or at least about 15 weight percent, or at least about 20 weight percent, or at least about 25 weight percent, or at least about 30 weight percent, or at least about 35 weight percent, or at least about 40 weight percent, or at least about 45 weight percent, or at least about 50 weight percent, and so on, in increments of 1 weight percent (i.e., 2, 3, 4, 5, . . . ) up to or at least about 95 weight percent or higher of the total lipids in the oil, composition of formulation. Other LCPUFAs (e.g., DPAn-6, DPAn-3, DTAn-6, DHA and/or EPA) can also be included in an amount that is at least about 2 weight percent, or at least about 5 weight percent, or at least about 10 weight percent, or at least about 15 weight percent, or at least about 20 weight percent, or at least about 25 weight percent, or at least about 30 weight percent, or at least about 35 weight percent, or at least about 40 weight percent, or at least about 45 weight percent, or at least about 50 weight percent, and so on, in increments of 1 weight percent (i.e., 2, 3, 4, 5, . . . ) up to or at least about 95 weight percent or higher of the total lipids in the oil, composition, formulation or other product.

In another preferred embodiment, the oil, composition, formulation or other product comprises about 30 weight percent or more, about 35 weight percent or more, about 40 weight percent or more, about 45 weight percent or more, about 50 weight percent or more, about 55 weight percent or more, about 60 weight percent or more, about 65 weight percent or more, about 70 weight percent or more, about 75 weight percent or more, or about 80 weight percent or more, or about 85 weight percent or more, or about 90 weight percent or more, or about 95 weight percent or more of a combination of SDA and/or GLA with DPAn-6, DHA, or combinations of DPAn-6 and DHA. Preferably, the ratio of SDA or GLA to DHA and/or DPA (n-6) in the oil, composition, formulation or other product is between about 1:10 to about 10:1, or any ratio between 1:10 and 10:1.

Forms of Provision of LCPUFAs and Oxylipins

In accordance with the present invention, the LCPUFAs (e.g., SDA and/or GLA, alone or in combination with other LCPUFAs) and/or oxylipin derivatives thereof that are used in oils, supplements, cosmetics, therapeutic compositions, and other formulations or products described herein are provided in a variety of forms. For example, such forms include, but are not limited to: an algal oil comprising the LCPUFAs and/or oxylipin derivatives thereof, preferably produced as described herein; a plant oil comprising the LCPUFA and/or oxylipin derivatives thereof, preferably produced as described herein; triglyceride oil comprising the LCPUFA; phospholipids comprising the LCPUFA; a combination of protein, triglyceride and/or phospholipid comprising the LCPUFA; dried marine microalgae comprising the LCPUFA; sphingolipids comprising the LCPUFA; esters of the LCPUFA; free fatty acid; a conjugate of the LCPUFA with another bioactive molecule; and combinations thereof. Long chain fatty acids can be provided in amounts and/or ratios that are different from the amounts or ratios that occur in the natural source of the fatty acids, such as by blending, purification, enrichment (e.g., through culture and/or processing techniques) and genetic engineering of the source. Bioactive molecules can include any suitable molecule, including, but not limited to, a protein, an amino acid (e.g. naturally occurring amino acids such as DHA-glycine, DHA-lysine, or amino acid analogs), a drug, and a carbohydrate. The forms outlined herein allow flexibility in the formulation of foods with high sensory quality, dietary or nutritional supplements, and pharmaceutical agents.

In one embodiment of the invention, a source of the desired phospholipids includes purified phospholipids from eggs, plant oils, and animal organs prepared via extraction by polar solvents (including alcohol or acetone) such as the Friolex process and phospholipid extraction process (PEP) (or related processes) for the preparation of oils or compositions (nutritional supplements, cosmetics, therapeutic formulations) rich in SDA and/or GLA or oxylipins derived therefrom, alone or in combination with other LCPUFAs (e.g., DHA, EPA, DPAn-6, DPAn-3, DTAn-6) and/or oxylipins derived therefrom. The Friolex and related processes are described in greater detail in PCT Patent Nos. PCT/IB01/00841, entitled "Method for the Fractionation of Oil and Polar Lipid-Containing Native Raw Materials", filed Apr. 12, 2001, published as WO 01/76715 on Oct. 18, 2001; PCT/IB01/00963, entitled "Method for the Fractionation of Oil and Polar Lipid-Containing Native Raw Materials Using Alcohol and Centrifugation", filed Apr. 12, 2001, published as WO 01/76385 on Oct. 18, 2001; and PCT/DE95/01065 entitled "Process For Extracting Native Products Which Are Not Water-Soluble From Native Substance Mixtures By Centrifugal Force", filed Aug. 12, 1995, published as WO 96/05278 on Feb. 22, 1996; each of which is incorporated herein by reference in its entirety. Methods for the production and use of a polar lipid-rich fraction containing omega-3 and/or omega-6 highly unsaturated fatty acids from microbes, genetically modified plant seeds and marine organisms is described in PCT Publication No. WO 02/092540, published Nov. 21, 2002, and methods for the production and use of a polar lipid-rich fraction containing stearidonic acid and gamma linolenic acid from plant seeds and microbes are described in detail in PCT Publication No. WO 02/092073, published Nov. 21, 2002, each incorporated herein by reference in its entirety.

Any biologically acceptable dosage forms, and combinations thereof, are contemplated by the inventive subject matter. Examples of such dosage forms include, without limitation, chewable tablets, quick dissolve tablets, effervescent tablets, reconstitutable powders, elixirs, liquids, solutions, suspensions, emulsions, tablets, multi-layer tablets, bi-layer tablets, capsules, soft gelatin capsules, hard gelatin capsules, caplets, lozenges, chewable lozenges, beads, powders, granules, particles, microparticles, dispersible granules, cachets, douches, suppositories, creams, topicals, inhalants, aerosol inhalants, patches, particle inhalants, implants, depot implants, ingestibles, injectables, infusions, health bars, confections, cereals, cereal coatings, foods, nutritive foods, functional foods and combinations thereof. The preparations of the above dosage forms are well known to persons of ordinary skill in the art. Preferably, a food (food product) that is enriched with the desired LCPUFAs and/or oxylipin derivatives thereof is selected from the group including, but not limited to: baked goods and mixes; chewing gum; breakfast cereals; cheese products; nuts and nut-based products; gelatins, pudding, and fillings; frozen dairy products; milk products; dairy product analogs; hard or soft candy; soups and soup mixes; snack foods; processed fruit juice; processed vegetable juice; fats and oils; fish products; plant protein products; poultry products; and meat products.

More particularly, oils containing LCPUFAs and oxylipin derivatives thereof, and particularly, enhanced levels of LCPUFA oxylipins (and in particular SDA- and/or GLA-derived oxylipins), will be useful as dietary supplements in the form of oil-filled capsules or through fortification of foods, beverages or infant formula to enhance the anti-inflammatory benefits of these products and/or promote more balanced immune function over that achieved by an LCPUFA oil with low or no LCPUFA oxylipin (and in particular SDA- and/or GLA-derived oxylipin) content. For example, LCPUFA oxylipin (and in particular SDA- and/or GLA-derived oxylipin)-enriched LCPUFA oils capsules, and preferably gelatin capsules for protection against oxidation, are provided for delivery of both the LCPUFA(s) and enhanced LCPUFA oxylipin (and in particular SDA- and/or GLA-derived oxylipin) content in a single dietary supplement. In another application, foods and beverages, including but not limited to dairy products and dairy analogs, bakery products and confectionaries, processed meats and meat analogs, grain products and cereals, liquid and powered beverages, including juices and juice drinks, carbonated and processed beverage products or infant formulas would be fortified with LCPUFA oils with enhanced levels of LCPUFA oxylipins (and in particular SDA- and/or GLA-derived oxylipin) and thereby increase the LCPUFA oxylipin (and in particular SDA- and/or GLA-derived oxylipin) intake over the non-LCPUFA oxylipin (and in particular SDA- and/or GLA-derived oxylipin)-enriched LCPUFA oils alone. In another example, LCPUFA oxylipin (and in particular SDA- and/or GLA-derived oxylipin)-enriched LCPUFA oils could be microencapsulated prior to fortification of the foods, beverages or formulas to reduce oxidation/degradation of the LCPUFA oxylipins (and in particular SDA- and/or GLA-derived oxylipins) and/or LCPUFA and improve organoleptic properties and shelf-life of the fortified food/beverage or infant formula products. In another example, LCPUFA oxylipin (and in particular SDA- and/or GLA-derived oxylipin)-enriched oils could be formulated into a cream or emulsion for topical applications for reduction of inflammation, or the LCPUFA oxylipin (and in particular SDA- and/or GLA-derived oxylipin)-enriched oils could be formulated into sun screens or cosmetics, such as face or hand creams, moisturizers, foundations, eye gels or shaving creams, to reduce skin irritation or redness, allergic reactions, or puffiness/edema. In another example, more highly enriched or purified forms of the LCPUFA oxylipins (and in particular SDA- and/or GLA-derived oxylipins) or LCPUFA oxylipin (and in particular SDA- and/or GLA-derived oxylipin)-rich oils could be used in pharmaceutical formulations to prevent or reduce symptoms of conditions or diseases associated with local, systemic, chronic or acute inflammatory reactions or processes.

Additional Components

In one embodiment of the present invention, any of the sources of LCPUFAs and/or oxylipin derivatives thereof (and preferably SDA and/or GLA and/or the oxylipin derivatives of either of these LCPUFAs), including any oils or compositions or formulations containing such LCPUFAs or oxylipin derivatives thereof, can be provided with one or more additional components that may be useful in a method of the invention. Such additional components include, but are not limited to, any additional anti-inflammatory agent, nutritional supplement (e.g., vitamins, minerals and other nutritional agents, including nutraceutical agents), a therapeutic agent, or a pharmaceutical or a nutritional carrier (e.g., any excipient, diluent, delivery vehicle or carrier compounds and formulations that can be used in conjunction with pharmaceutical (including therapeutic) compositions or nutritional compositions).

In one preferred embodiment, the LCPUFAs and/or oxylipin derivatives thereof are provided along with acetosalicylic acid (ASA), or aspirin or any other anti-inflammatory agent.

Methods to Produce and Optimize Production of LCPUFAs and LCPUFA-derived Oxylipins Methods for producing LCPUFA-containing oils using microbial technology have been taught in the art. U.S. Pat. No. 5,130,242 and U.S. Pat. No. 5,340,594 teach methods for producing DHA and DPA rich lipids via fermentation using *Schizochytrium* spp. or *Thraustochytrium* spp. U.S. Patent Application Publication No. 2003/0161866 describes a process for preparing oils containing DHA and DPAn-6 by cultivating a microorganism belonging to the presumptive genus

*Ulkenia*. Such microorganisms can be further genetically modified to produce LCPUFAs such as SDA or GLA. Some algae naturally comprise up to 20% SDA (as a percentage of total fatty acids), and some fungi naturally comprise up to 20-27% GLA (as a percentage of total fatty acids).

Methods for producing LCPUFA-containing plants and plant seed oils have been described in, for example, U.S. Pat. No. 6,566,583; U.S. Patent Application Publication No. 20020194641, U.S. Patent Application Publication No. 20040235127A1, and U.S. Patent Application Publication No. 20050100995A1, as well as Napier and Sayanova, *Proceedings of the Nutrition Society* (2005), 64:387-393; Robert et al., *Functional Plant Biology* (2005) 32:473-479; or U.S. Patent Application Publication 2004/0172682. In addition, borage oil naturally comprises up to 20-24% GLA, evening primrose oil naturally comprises up to 9-10% GLA, black current oil naturally comprises up to 15-17% GLA, and echium oil naturally comprises up to 8-14% SDA and 7-12% GLA.

Methods of producing LCPUFA-containing fish oils are also well known in the art. Fish oils, such as from sources listed previously herein, naturally comprise up to 4-7% SDA.

As discussed above, oxylipins useful in the present invention can be produced through chemical synthesis using LCPUFA precursors or can be synthesized completely de novo. Chemical synthesis methods for oxylipin compounds are known in the art (e.g., see Rodriguez and Spur (2004); Rodriguez and Spur, 2005; Guilford et al. (2004)). In addition, general chemical synthesis methods are well known in the art. For example, the compounds of present invention may be prepared by both conventional and solid phase synthetic techniques known to those skilled in the art. Useful conventional techniques include those disclosed by U.S. Pat. Nos. 5,569,769 and 5,242,940, and PCT publication No. WO 96/37476, all of which are incorporated herein in their entirety by this reference. Combinatorial synthetic techniques, however, may be particularly useful for the synthesis of the compounds of the present invention. See, e.g., Brown, *Contemporary Organic Synthesis*, 1997, 216; Felder and Poppinger, *Adv. Drug Res.*, 1997, 30, 111; Balkenhohl et al., *Angew. Chem. Int. Ed. Engl.*, 1996, 35, 2288; Hermkens et al., *Tetrahedron*, 1996, 52, 4527; Hermkens et al., *Tetrahedron*, 1997, 53, 5643; Thompson et al., *Chem. Rev.*, 1996, 96, 555; and Nefzi et al., *Chem. Rev.*, 1997, 2, 449-472.

The compounds of the present invention can be synthesized from readily available starting materials. Various substituents on the compounds of the present invention can be present in the starting compounds, added to any one of the intermediates or added after formation of the final products by known methods of substitution or conversion reactions. If the substituents themselves are reactive, then the substituents can themselves be protected according to the techniques known in the art. A variety of protecting groups are known in the art, and can be employed. Examples of many of the possible groups can be found in "Protective Groups in Organic Synthesis" by T. W. Green, John Wiley and Sons, 1981, which is incorporated herein in its entirety. For example, nitro groups can be added by nitration and the nitro group can be converted to other groups, such as amino by reduction, and halogen by diazotization of the amino group and replacement of the diazo group with halogen. Acyl groups can be added by Friedel-Crafts acylation. The acyl groups can then be transformed to the corresponding alkyl groups by various methods, including the Wolff-Kishner reduction and Clemmenson reduction. Amino groups can be alkylated to form mono- and di-alkylamino groups; and mercapto and hydroxy groups can be alkylated to form corresponding ethers. Primary alcohols can be oxidized by oxidizing agents known in the art to form carboxylic acids or aldehydes, and secondary alcohols can be oxidized to form ketones. Thus, substitution or alteration reactions can be employed to provide a variety of substituents throughout the molecule of the starting material, intermediates, or the final product, including isolated products.

Since the compounds of the present invention can have certain substituents which are necessarily present, the introduction of each substituent is, of course, dependent on the specific substituents involved and the chemistry necessary for their formation. Thus, consideration of how one substituent would be affected by a chemical reaction when forming a second substituent would involve techniques familiar to one of ordinary skill in the art. This would further be dependent upon the ring involved.

Alternatively, the oxylipins are catalytically produced via an enzyme-based technology using LCPUFAs (e.g., SDA or GLA) as the substrate. In one embodiment, enzymes such as lipoxygenases, cyclooxygenases, cytochrome P450 enzymes and other heme-containing enzymes, such as those described in Table 1 (e.g., provided as recombinant or isolated/immobilized enzyme preparations) are contacted in vitro with the LCPUFAs produced by an organism, such as during extraction or post-harvest processing of a microorganism biomass or plant or oilseed or animal, whereby LCPUFAs produced by the organism are converted to oxylipins. The oxylipin derivatives of LCPUFAs can also be produced by microorganisms in a fermentor and recovered and purified for use. Preferred methods of production and recovery of oxylipins which are believed to enhance the quantity, quality and stability of the compounds are described below. The oxylipins produced by any of the above production technologies, can be further processed and recovered as derivatives of the oxylipins or salts thereof to aid in the recoverability, stability, absorption, bioavailability and/or efficacy, if desired. In addition, the oxylipins produced by any of the technologies described herein can be used to supplement other sources of oxylipins (e.g., a refined LCPUFA oil) or provided in the form of any composition or formulation for use in any application described herein.

Methods to Optimize Production of LCPUFA Oxylipin Concentrations in Oils Produced by Organisms The production or fermentation conditions can be optimized to enhance production of the LCPUFA oxylipins (and in particular SDA- and/or GLA-derived oxylipins) and/or to stabilize them once they have been produced. These methods include selecting culture conditions that enhance activity and/or expression of the enzymes producing these compounds. For example, any culture condition that alters the cell concentration and/or specific growth rate of the culture can potentially alter the cellular composition. Culture conditions that are known to modify the production of metabolites or secondary metabolites in microorganisms include but are not limited to the following: hypoosmotic or hyperosomotic salinity stress, nutrient limitation stress (such as nitrogen, phosphorus, carbon, and/or trace metals), temperature stress (higher or lower than customary), elevated or reduced levels of oxygen and/or carbon dioxide, and physical stresses such as shear. In addition, the level of metabolites or secondary metabolites in cells can vary with phase of growth (exponential vs stationary), and by providing various precursor molecules for bioconversion by the microorganism.

These methods also include use of additives, both organic and inorganic, which enhance this enzymatic activity, or alternatively, directly enhance auto-oxidation of the LCPUFAs to these compounds and/or stabilize the LCPUFA oxylipins (and in particular SDA- and/or GLA-derived oxylipins) once they are produced. For example, compounds that modify or acetylate COX2 (such as one of the many forms of acetylsalicylic acid) or compounds which stimulate expression or activity of COX2, lipoxygenase, cytochrome P450 enzymes (including hydroxylases, peroxidases, and oxygenases) and/or other heme-containing enzymes, can be added to the culture medium. Examples of compounds that may enhance the expression or activity of lipoxygenases, cyclooxygenases, cytochrome P450 and other heme-containing enzymes in culture include, but are not limited to: ATP, cytokines (e.g., interleukin-4, interleukin-13, or granulocyte-macrophage colony-stimulating factor), hormones (e.g., bradykinin or 1,25-dihydroxyvitamin $D_3$), cationic metals (e.g., $Ca^{2+}$), phospholipids (e.g., phosphatidyl serine), fatty acids (e.g., DHA), preformed hydroperoxides, glucocorticoids (e.g., dexamethasone), nonsteroidal anti-inflammatory compounds (e.g., acetosalicylic acid or aspirin), and other inducers of cytochrome P450 activities (e.g., ethanol, fibrates and other peroxisome proliferators, phenobarbital, steroids, and rifampicin). Additionally, compounds or conditions that lead to autooxidation of the LCPUFAs in the microorganism resulting in formation of the mono- thru penta-hydroxy derivatives of these LCPUFA are also preferred. For example, such compounds or conditions that can promote autooxidation of LCPUFAs include, but are not limited to, metals (including transition metals such as iron, copper or zinc, and alkali earth metals such as magnesium), peroxides, lipid radicals, and high oxygen conditions.

Improved Oil Extraction Processes that Enhance LCPUFA Oxylipin Content or Retention As enzymes play an important role in the formation of hydroxy derivatives of LCPUFAs, there are preferable methods for enhancing contact between these enzymes and the LCPUFAs to enhance formation of the hydroxy derivatives. In one preferred process, the microbial cells or oilseeds are ruptured (e.g., via homogenization for the microbial cells or by crushing for the oilseeds) and the resulting oil and biomass mixture is allowed to incubate for a period of time under optimal conditions (e.g., temperature, pH, residual water activity, ion concentration and presence of any necessary cofactors) to allow the enzymes liberated in the biomass to react directly with the LCPUFAs. Similarly, auto-oxidation processes can be facilitated in this manner.

Modification of Oil Processing Conditions

Preferred oil processing methods include methods that are focused on minimally processing the oil. Processes used in conventional oilseed processing tend to remove free fatty acids or free fatty acid-like compounds and thereby remove the fatty acid-like hydroxy derivatives of LCPUFAs. In particular, caustic treatments of the oils focused on removal of free fatty acids (commonly referred to as refining the oil), should be avoided. Preferably the oil is extracted with an alcohol (e.g. isopropyl alcohol) or other organic solvent (e.g. hexane), or mixtures thereof, or supercritical fluids (e.g. carbon dioxide) and the resulting oil is chill filtered, bleached, chill filtered again and then deodorized. In a more preferable method the chill filtration steps are eliminated and the oil is simply bleached and deodorized after extraction. In an even more preferable method, the only processing step after extraction of the oil is limited to deodorization of the oil. In the above extractions, alcohols or alcohol water mixtures are preferable for use in extracting the oil rather than using organic solvents such as hexane. As an alternative to chemical extraction, oils may be separated from the biomass through expeller pressing, or disruption followed by centrifugation, using a separating processing aid such as a primary alcohol or carrier oil. These crude oils may be purified and stabilized through one or more of the methods described above.

Methods for Further Processing LCPUFA oil (microbial, plant, fish) to Enhance and/or Stabilize LCPUFA Oxylipin Content In one preferred method, once the oils have been extracted and processed by the methods described above or by any other suitable method, antioxidants can be added to the oil to help stabilize the LCPUFA oxylipins (and in particular SDA- and/or GLA-derived oxylipins) in the oil. In another preferred method, antioxidants may be added at one or more points in the extraction and purification process to minimize potential oxidative degradation of oxylipins and/or LCPUFAs. In addition, the oxylipins will become more polar molecules as more hydroxy groups are incorporated into them, the oil can be prepared in an emulsion form to enhance content/solubility/stability of both polar and less polar forms of the LCPUFA oxylipins (and in particular SDA- and/or GLA-derived oxylipins) and facilitate their use in, e.g., a wider variety of food and pharmaceutical applications than those available to use of an oil ingredient form alone.

In a preferable downstream process, an LCPUFA-rich oil (microbial-, plant- or animal (including fish)-based) or hydrolyzed or saponified form of the oil, and particularly an SDA- and/or GLA-derived oxylipin-rich oil, can be processed in an enzyme-based reaction system (e.g. column or stirred tank reactor) to facilitate the enzymatic production of the LCPUFA oxylipins (and in particular SDA- and/or GLA-derived oxylipins) in the oil. In one embodiment, after saponification, LCPUFA free fatty acids are separated from saturated and monounsaturated fats by distillation or precipitation techniques (or other suitable techniques), for example, and then reacted with the enzyme-based system. The enzymes can be present in either free or immobilized forms in these systems. Exemplary enzymes (including lipoxygenases, cyclooxygenases, cytochrome P450 enzymes and other heme-containing enzymes) that can be utilized in these systems are listed in Table 1. Reaction conditions, such as temperature, pH, residual water activity, ion concentration and presence of cofactors, can be chosen to maximize the rate and extent of conversion of PUFAs to lipoxins. The oil can be processed through the column/reactor either in the oil form or as hydrolyzed free fatty acids, which are produced by hydrolyzing the PUFA-containing triglycerides in the oil to convert the PUFAs from an esterified to a free acid form.

In one embodiment of the invention, any of the oils produced by any of the methods described herein can be further processed to separate or purify the LCPUFA oxylipins from the LCPUFAs in the oil. This process can be performed on oils that have been processed by any refinement process, including oils or products thereof that have been treated to convert LCPUFAs in the oil to oxylipin derivatives. For example, LCPUFA oxylipins can be separated from LCPUFAs by any suitable technique, such as any chromatography technique, including, but not limited to, silica gel liquid chromatography. In one embodiment, LCPUFA oxylipins produced, enriched or purified by the processes of the present invention (including any of the production/processing methods described herein and/or de novo synthesis) can be added back to (titrated into) another oil, such as an LCPUFA oil produced by any method, and/or can be added to any composition or formulation or other product.

After the oils/fatty acids (which include oxylipins derived therefrom) have been processed in this manner, the oil/fatty acids can be used directly in food, pharmaceutical or cosmetic applications or can be used to add (by blending) to LCPUFA or non-LCPUFA-containing oils to enhance their content of LCPUFA oxylipins (and in particular SDA- and/or GLA-derived oxylipins). In this manner, a consistent LCPUFA oxylipin (and in particular SDA- and/or GLA-derived oxylipins) content of the final oil product can be achieved.

When using lipoxygenase enzymes in these types of systems, up to 100% of the target LCPUFA can be transformed into their hydroxy derivatives. An example of such a system would be an immobilized enzyme column containing immobilized 15-lipoxygenase. When SDA is processed thru this system, the SDA is transformed to the hydroperoxides 13-hydroperoxy SDA and 6,13-di-hydroperoxy SDA, which can then be transformed into the hydroxy derivatives 13-hydroxy SDA and 6,13-dihydroxy SDA, following reduction with an agent such as $NaBH_4$. This concentrated form of LCPUFA oxylipins (and in particular SDA- and/or GLA-derived oxylipins) can then be titrated into an appropriate edible oil to achieve the desired LCPUFA oxylipin (and in particular SDA- and/or GLA-derived oxylipins) content in the final oil.

Applications of SDA, GLA, SDA-Derived Oxylipins and/or GLA-Derived Oxylipins and Oils or Compositions Comprising SDA, GLA, SDA-Derived Oxylipins and/or GLA-Derived Oxylipins and/or any other LCPUFA Oxylipins The present invention is based on the use of LCPUFAs comprising SDA and/or GLA and/or the oxylipin derivatives thereof, and/or various oils that have been enriched for oxylipin derivatives of SDA and/or GLA, and in some embodiments, also for the oxylipin derivatives of C20 and greater PUFAs, and particularly for docosanoids, to provide anti-inflammatory, anti-proliferative, neuroprotective and/or vasoregulatory effects in humans and other animals. Such effects are useful for enhancing the general health of an individual, as well as in treating or preventing a variety of diseases and conditions in an individual. For example, the invention includes methods for treating metabolic imbalances and disease states that could benefit from the modulation of inflammation provided by the LCPUFA- and/or oxylipin-, and particularly, SDA- or GLA-derived oxylipin-, containing compositions and oils described herein.

Additional applications encompassed by the present invention for the use of any of the LCPUFA and/or oxylipin-containing oils, compositions or formulations described herein (preferably including SDA, GLA and/or oxylipin derivatives thereof, as well as oils and products produced with such oils that are enriched for oxylipin derivatives), include, but are not limited to, the following: (1) $Rh^+$ incompatibility during pregnancy; (2) inflammatory diseases of the bowel and gastrointestinal tract (e.g. Crohn's, inflammatory bowel disease, colitis, and necrotizing enterocolitis in infants); (3) autoimmune diseases (e.g. insulin-dependent diabetes mellitus (Type I diabetes), multiple sclerosis, rheumatoid arthritis, systemic lupus erythematosus, myasthenia gravis, celiac disease, autoimmune thyroiditis, Addison's disease, Graves' disease and rheumatic carditis); (4) chronic adult-onset diseases that involve inflammation (e.g. cardiovascular disease, Type II diabetes, age-related macular degeneration, atopic diseases, metabolic syndrome, Alzheimer's disease, cystic fibrosis, colon cancer, etc.); (5) inflammatory diseases of the skin (e.g., dermatitis (any form), eczema, psoriasis, rosacea, acne, pyoderma gangrenosum, urticaria, etc.); (6) inflammatory diseases of the eye; and (7) inflammation due to infectious diseases (bacteria, fungal, viral, parasitic, etc.). Many of these are diseases in which patients may not want to be on steroids or non-specific anti-inflammatory drugs because of negative side effects.

Accordingly, one embodiment of the present invention relates to the use of: (1) SDA, GLA and/or an oxylipin derivative thereof, alone or in combination with each other and/or with other LCPUFAs and/or oxylipin derivatives thereof (preferably DPAn-6, DPAn-3, DTAn-6, DHA and/or EPA, and most preferably, DPAn-6 and/or DHA); and/or (2) an oil or product produced using such oil, wherein the oil has been enriched in quantity, quality and/or stability of the LCPUFA oxylipins contained therein, and preferably the SDA-derived or GLA-derived oxylipins. The use of these compositions is typically provided by an oil or product using such oil, a nutritional supplement, cosmetic formulation or pharmaceutical composition (medicament or medicine). Such oils, supplements, compositions and formulations can be used for the reduction of inflammation in a patient that has or is at risk of developing inflammation or a disease or condition associated with inflammation. Such oils, supplements, compositions and formulations can also be used for the reduction of any symptoms related to neurodegeneration or a disease associated with neurodegeneration in a patient that has or is at risk of developing a neurodegenerative condition or disease. In particular, the patient to be treated using the composition of the invention has inflammation associated with the production of eicosanoids and/or what are generally termed in the art as "proinflammatory" cytokines. Such cytokines include, but are not limited to, interleukin-1α (IL-1α), IL-1β, tumor necrosis factor-α (TNFα), IL-6, IL-8, IL-12, macrophage inflammatory protein-1α (MIP-1α), macrophage chemotactic protein-1 (MCP-1) and interferon-γ (IFN-γ). The patient is administered a composition comprising an amount of such LCPUFAs and/or oxylipin derivatives thereof in an amount effective to reduce at least one symptom of inflammation or neurodegeneration in the patient.

Symptoms of inflammation include both physiological and biological symptoms including, but are not limited to, cytokine production, eicosanoid production, histamine production, bradykinin production, prostaglandin production, leukotriene production, fever, edema or other swelling, pain (e.g., headaches, muscle aches, cramps, joint aches), chills, fatigue/loss of energy, loss of appetite, muscle or joint stiffness, redness of tissues, fluid retention, and accumulation of cellular mediators (e.g., neutrophils, macrophages, lymphocytes, etc.) at the site of inflammation. Diseases associated with inflammation include, but are not limited to, conditions associated with infection by infectious agents (e.g., bacteria, viruses), shock, ischemia, cardiopulmonary diseases, autoimmune diseases, neurodegenerative conditions, and allergic inflammatory conditions, and various other diseases detailed previously herein.

Symptoms associated with neurodegeneration include both physiological and biological symptoms including, but not limited to: neurodegeneration, intellectual decline, behavioral disorders, sleep disorders, common medical complications, dementia, psychosis, anxiety, depression, inflammation, pain, and dysphagia. Neurodegenerative diseases that may be treated using the oxylipin derivatives and compositions of the invention include, but are not limited to: schizophrenia, bipolar disorder, dyslexia, dyspraxia, attention deficit hyperactivity disorder (ADHD), epilepsy, autism, Alzheimer's Disease, Parkinson's Disease, senile dementia, peroxisomal proliferator activation disorder (PPAR), multiple sclerosis, diabetes-induced neuropathy, macular degeneration, retinopathy of prematurity, Huntington's Disease, amyotrophic lateral sclerosis (ALS), retinitis pigmentosa, cerebral palsy, muscular dystrophy, cancer, cystic fibrosis, neural tube defects, depression, Zellweger syndrome, Lissencepahly, Down's Syndrome, Muscle-Eye-Brain Disease, Walker-Warburg Syndrome, Charoct-Marie-Tooth Disease, inclusion body myositis (IBM) and Aniridia.

In one embodiment of the present invention, the novel SDA- and/or GLA-derived oxylipins of the invention, and/or oils or compositions containing such SDA- and/or GLA-derived oxylipins are used to selectively target the particular proinflammatory cytokines and conditions or diseases associated with the production of these cytokines. Based on the prior observation by the present inventors that particular docosanoids selectively inhibit certain cytokines and inflammatory conditions, the inventors propose that the novel oxylipins of the present invention can also be used in particular conditions or diseases to provide a more selective treatment of an individual and avoid side effects that may be associated with more global inhibition of inflammatory processes. For example, the present inventors have shown that the DPAn-6 docosanoids, 17-hydroxy DPAn-6 and 10,17-dihydroxy DPAn-6, significantly reduced secretion of the potent proinflammatory cytokine IL-13, with the reduction produced by 10,17-dihydroxy DPAn-6 being significantly larger than with that produced by either the DHA oxylipin derivative or the general anti-inflammatory agent, indomethacin (see U.S. Patent Publication No. 2006/0241088, supra). Even more striking were the observed differences between the activities of two different oxylipin derivatives of DPAn-6. As shown in that application, while both 17-HDPAn-6 and 10,17-dihydroxy DPAn-6 are demonstrated to be potent anti-inflammatory agents, there were differences between the activity of these two DPAn-6 oxylipins in their effect on cytokine production (e.g., IL-13), indicating that one compound may be more suitable than the other for specific applications (e.g., sepsis versus swelling). Specifically, 17-HDPAn-6 was more potent than the DHA-derived oxylipin for inhibiting cell migration, and 10,17-dihydroxy DPAn-6 was more potent than the DHA oxylipin for reduction in IL-13 secretion. Similar characteristics may be expected from the SDA- and GLA-derived oxylipins of the present invention. Therefore, one of skill in the art can select oxylipins of the present invention for specific uses, and reduce the potential side effects of a treatment as compared to using more pan-specific or generic anti-inflammatory agents.

The compositions and method of the present invention preferably protect the patient from inflammation, or a condition or disease associated with inflammation. As used herein, the phrase "protected from a disease" (or symptom or condition) refers to reducing the symptoms of the disease; reducing the occurrence of the disease, and/or reducing the severity of the disease. Protecting a patient can refer to the ability of a nutritional or therapeutic composition of the present invention, when administered to the patient, to prevent inflammation from occurring and/or to cure or to alleviate inflammation and/or disease/condition symptoms, signs or causes. As such, to protect a patient from a disease or condition includes both preventing occurrence of the disease or condition (prophylactic treatment) and treating a patient that has a disease or condition or that is experiencing initial symptoms of a disease or condition (therapeutic treatment). The term, "disease" or "condition" refers to any deviation from the normal health of an animal and includes a state when disease symptoms are present, as well as conditions in which a deviation (e.g., infection, gene mutation, genetic defect, etc.) has occurred, but symptoms are not yet manifested.

According to the present invention, the oxylipins (or analogs or derivatives thereof), compositions comprising such oxylipins, and methods of the invention, are suitable for use in any individual (subject) that is a member of the Vertebrate class, Mammalia, including, without limitation, primates, livestock and domestic pets (e.g., a companion animal). Most typically, an individual will be a human. According to the present invention, the terms "patient", "individual" and "subject" can be used interchangeably, and do not necessarily refer to an animal or person who is ill or sick (i.e., the terms can reference a healthy individual or an individual who is not experiencing any symptoms of a disease or condition). In one embodiment, an individual to which an oxylipin(s) or composition or formulation or oil of the present invention can be administered includes an individual who is at risk of, diagnosed with, or suspected of having inflammation or neurodegeneration or a condition or disease related thereto. Individuals can also be healthy individuals, wherein oxylipins or compositions of the invention are used to enhance, maintain or stabilize the health of the individual.

The amount of an LCPUFA or oxylipin derivative thereof to be administered to a individual can be any amount suitable to provide the desired result of reducing at least one symptom of inflammation or neurodegeneration or protecting the individual from a condition or disease associated with such inflammation or neurodegeneration. In one embodiment, an LCPUFA such as SDA is administered in a dosage of from about 0.5 mg of the PUFA per kg body weight of the individual to about 200 mg of the PUFA per kg body weight of the individual, although dosages are not limited to these amounts. An LCPUFA oxylipin derivative or mixture of oxylipin derivatives is administered in a dosage of from about 0.2 ug of the oxylipin per kg body weight of the individual to about 50 mg of the oxylipin per kg body weight of the individual, although dosages are not limited to these amounts.

Although compositions and formulations of the invention can be administered topically or as an injectable, the most preferred route of administration is oral administration. Preferably, the compositions and formulations used herein are administered to subjects in the form of nutritional supplements and/or foods (including food products) and/or pharmaceutical formulations and/or beverages, more preferably foods, beverages, and/or nutritional supplements, more preferably, foods and beverages, more preferably foods.

As discussed above, a variety of additional agents can be included in the compositions when administered or provided to the subject, such as other anti-inflammatory agents, vitamins, minerals, carriers, excipients, and other therapeutic agents. A preferred additional agent is aspirin, or another suitable anti-inflammatory agent.

The oxylipins (or analogs or derivatives or salts thereof), compositions comprising such oxylipins, and methods of the invention, are also suitable for use as feed ingredients, nutritional supplements or therapeutic agents in aquaculture applications in any individual (subject) that is a member of the Vertebrate class such as fish or for invertebrates such as shrimp.

The following experimental results are provided for purposes of illustration and are not intended to limit the scope of the invention.

EXAMPLES

Example 1

The following example demonstrates that stearidonic acid (SDA) can be completely converted to a mono-hydroxy and di-hydroxy derivative by 15-lipoxygenase.

FIG. 1 illustrates the major 15-lipoxygenase products of stearidonic acid (SDA, 18:4n-3). In this experiment, SDA (100 μM, NuChek Prep, Elysian, Minn.) was incubated with soybean 15-lipoxygenase (10 μg/ml, Sigma-Aldrich, St. Louis, Mo.) in 0.05M sodium borate buffer, pH 9.0, at 4° C. with vigorous stirring for 30 min. Reaction products were reduced with $NaBH_4$ (0.45 mg/ml) and then extracted on a solid phase C-18 cartridge (Supelco Discovery DSC-19) using anhydrous ethanol for elution. Reaction products were identified by LC/MS using an Agilent 1100 Series high performance liquid chromatograph (HPLC) interfaced with mass spectrometry detector. The HPLC was carried out on a Prodigy C18(2) column (250×4.6 mm, 5 micron, Phenomenex, Torrance Calif., USA) using a mobile phase consisting of 100 mM ammonium acetate in 30% methanol in water with an acetonitrile gradient increasing from 48 to 90% over 35 min (0.6 ml/min flow rate). The mass spectrometer was operated in the negative ion detection mode using fragmentor voltage of 120, with a mass range of 100 to 400 m/z. Nitrogen was used as nebulizing and drying gas. FIG. 1 depicts the structures of the major mono- and dihydroxy products of this SDA reaction.

Figure 5:
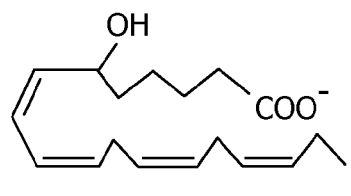
FIG. 5 depicts monohydroxy and dihydroxy derivatives of SDA.
Figure 5:
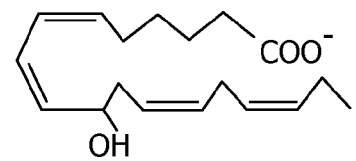
Figure 5:
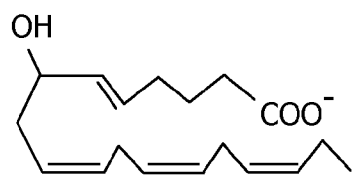
Figure 5:
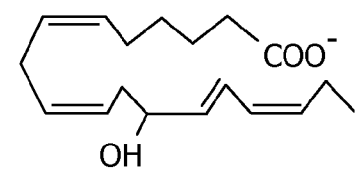
Figure 5:
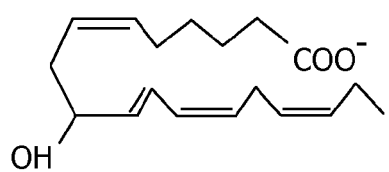
Figure 5:
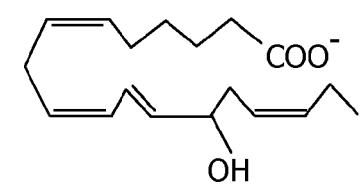
Figure 5:
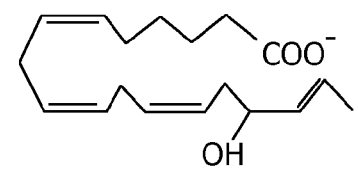
Figure 5:
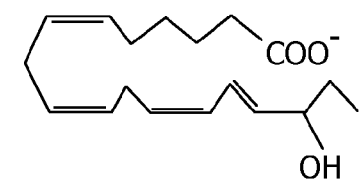
Figure 5:
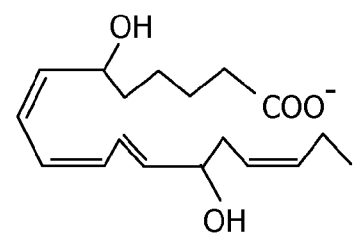
Figure 5:
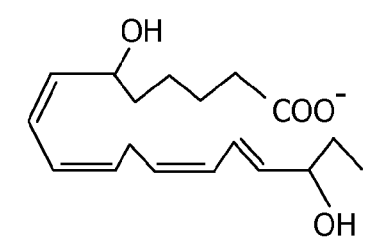

FIG. 5 illustrates various monohydroxy and dihydroxy products of SDA.

Example 2

The following example indicates the major 12-lipoxygenase products of SDA

Figure 2:
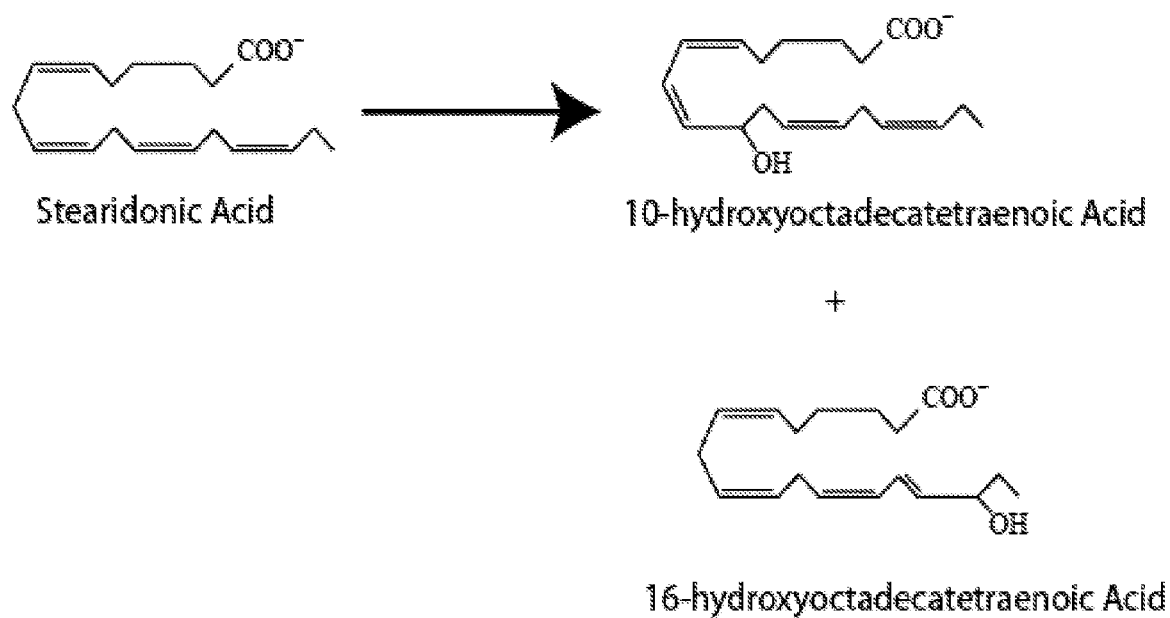
FIG. 2 depicts the structures of the major monohydroxy products of the reaction of SDA with 12-lipoxygenase.

SDA (30 μg/ml), Nu-Chek Prep (Elysian, Minn.) was incubated at room temperature (~23° C.) with 76 U of porcine 12-LOX (Cayman Chemical, Ann Arbor, Mich.)) in 0.1M TRIS-HCL, pH 7.5, 50 mM EDTA, 0.1% Tween 20 with vigorous stirring for 30 min. Reaction products were reduced with $NaBH_4$ (0.45 mg/ml), and the reaction product was then extracted on a solid phase C-18 cartridge (Supelco Discovery DSC-19) using anhydrous methanol for elution. The reaction mixture was analyzed by UV-VIS spectrophotometry and products of the reaction were further characterized using LC-MS-DAD, as described in Example 1. FIG. 2 depicts the structures of the major monohydroxy products of this SDA reaction.

Example 3

The following example indicates the major 5 lipoxygenase product of SDA.

Figure 3:
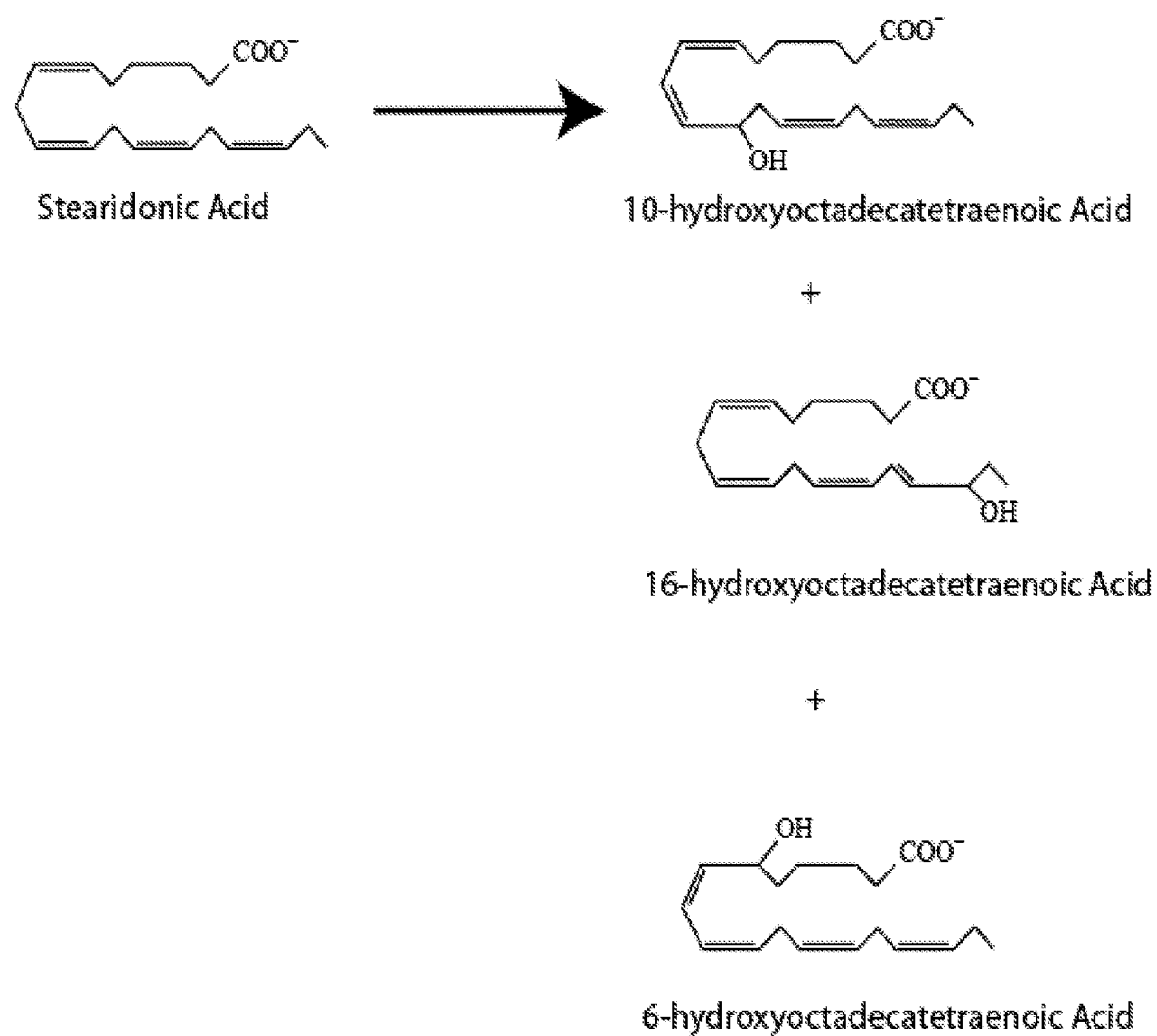
FIG. 3 depicts the major products of the reaction of SDA with 5-lipoxygenase.

To a 5 ml reaction mixture containing 200 μM SDA (Cayman Chemical, Ann Arbor, Mich.), in 0.1 M phosphate buffer, pH 6.3, and 5 mM EDTA, was added 420U of potato 5-lipoxygenase (5LOX) (Cayman Chemical (Ann Arbor, Mich.). The reaction mixture was stirred for 30 minutes at room temperature (~23° C.) and reaction products were reduced by addition of 1 ml of 0.5 mg/ml $NaBH_4$ (5 mg/ml in 1 M NaOH). The reaction was subsequently acidified with acetic acid and the products extracted using a solid phase C18 SPE cartridge and eluted with methanol. Reaction products were extracted using a solid phase C18 SPE cartridge and eluted with methanol. The reaction mixture was analyzed by UV-VIS spectrophotometry and products of the reaction were further characterized using LC-MS-DAD, as described in Example 1. The major reaction products are depicted in FIG. 3.

Example 4

The following example demonstrates that γ-linolenic acid (GLA) can be completely converted to mono-hydroxy and di-hydroxy derivatives by 15-lipoxygenase.

Figure 4:
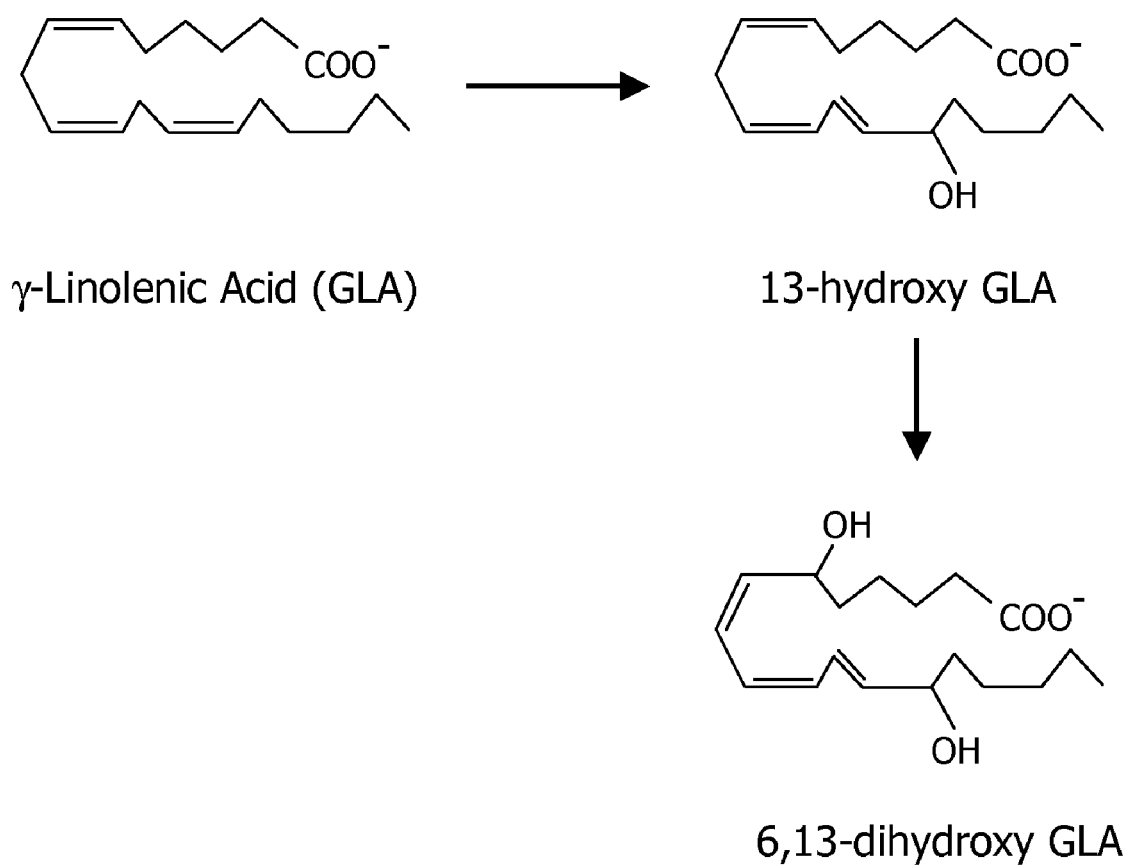
FIG. 4 depicts the structures of the major mono- and dihydroxy products of the reaction of GLA with 15-lipoxygenase.

FIG. 4 illustrates the major 15-lipoxygenase products of γ-linolenic acid (GLA, 18:3n-6). The reaction was carried out using 100 μM GLA (NuChek Prep, Elysian, Minn.) and reaction conditions and detection methods as described in Example 1. FIG. 2 depicts the structures of the major mono- and dihydroxy products of this GLA reaction.

Figure 6:
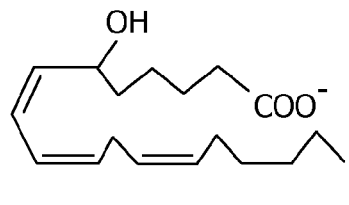
FIG. 6 depicts monohydroxy and dihydroxy derivatives of GLA.
Figure 6:
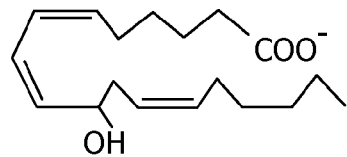
Figure 6:
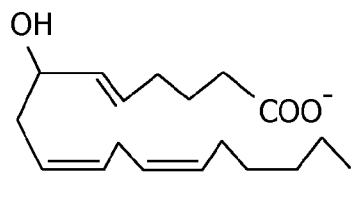
Figure 6:
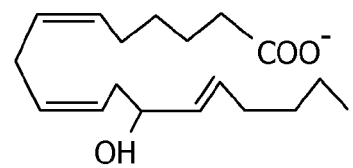
Figure 6:
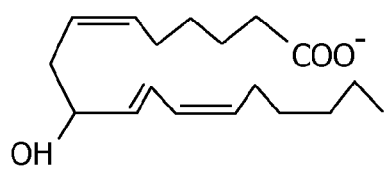
Figure 6:
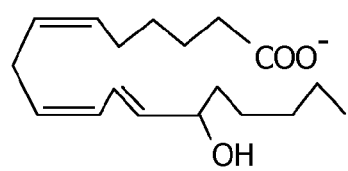
Figure 6:
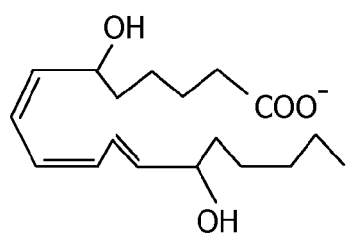

FIG. 6 illustrates various monohydroxy and dihydroxy products of GLA.

REFERENCES

Ariel et al (2005). The docosoatriene prototectin D1 is produced by Th2-skewing and promotes human T cell apoptosis via lipid-raft clustering. JBC Papers in Press, Manuscript M509796200.

Arita et al. (2005a). The contributions of aspirin and microbial oxygenase to the biosynthesis of anti-inflammatory resolvins: Novel oxygenase products from omega-3 polyunsaturated fatty acids. Biochem Biophys Res Commun. 2005 (in press)

Arita et al. (2005b). Resolvin E1, an endogenous lipid mediator derived from omega-3 eicosapentaenoic acid, protects against 2,4,6-trinitrobenzene sulfonic acid-induced colitis. Proc Natl Acad Sci USA, 102(21):7671-6.

Arita et al. (2005c). Stereochemical assignment, anti-inflammatory properties, and receptor for the omega-3 lipid mediator resolvin E1. J Exp Med. 201(5):713-22

Bannenberg et al. (2005a). Molecular circuits of resolution: formation and actions of resolvins and protectins. J. Immunol. 174(7):4345-55. Erratum in: J. Immunol. 2005 May 1; 174(9):5884.

Bannenberg et al. (2005b). Molecular circuits of resolution: formation and actions of resolvins and protectins. J. Immunol. 174(7):4345-55

Bazan (2005a). Lipid signaling in neural plasticity, brain repair, and neuroprotection. Mol. Neurobiol. 32(1):89-103.

Bazan (2005b). Neuroprotectin D1 (NPD1): a DHA-derived mediator that protects brain and retina against cell injury-induced oxidative stress. Brain Pathol. (2):159-66.

Bazan et al. (2005). Brain response to injury and neurodegeneration: endogenous neuroprotective signaling. Ann N Y Acad. Sci. 1053:137-47

Belayev et al. (2005). Docosahexaenoic acid complexed to albumin elicits high-grade ischemic neuroprotection. Stroke. 36(1):118-23.

Bouarab et al. (2004). The innate immunity of a marine red alga involves oxylipins from both the eicosanoid and octadecanoid pathways. Plant. Physiol. 135:1838-1848.

Butovich et al 2005. On the structure, synthesis and mechanism of formation of neuroprotectin D1-a novel anti-inflammatory compound of docosahexaenoic acid family. J Lipid Res. 2005 (in press)

Chen & Bazan (2005). Lipid signaling: sleep, synaptic plasticity, and neuroprotection. Prostaglandins Other Lipid Mediat. 77(1-4):65-76.

Flower and Perretti (2005). Controlling inflammation: a fat chance? Exp Med. 201(5):671-4.

Gerwick (1994). Structure and biosynthesis of marine algal oxylipins. Biochimica et Biophysica Acta 1221:243-255.

Gerwick & Bemart (1993). Eicosanoids and related compounds from marine algae. Pages 101-150 in, Zaborski and Attaway (eds) Marine Biotechnology Vol. 1: Pharmaceutical and bioactive products. Plenum Press, NY.

Gerwick et al. 1993. Biologically active oxylipins from seaweeds. Hydrobiologia 260/261:653-665.

Gilroy et al (2004). Inflammatory resolution: new opportunities for drug discovery. Nature Reviews 3:401-416.

Guilford et al (2004). Novel 3-oxa lipoxin A4 analogues with enhanced chemical and metabolic stability have anti-inflammatory activity in vivo. J Med. Chem. 2004 Apr. 8; 47(8):2157-65.

Hong et al. (2003). Novel docosatrienes and 17S-resolvins generated from docosahexaenoic acid in murine brain, human blood, and glial cells. Autacoids in anti-inflammation. J Biol Chem, 278(17):14677-87.

Lukiw et al. (2005). A role for docosahexaenoic acid-derived neuroprotectin D1 in neural cell survival and Alzheimer disease. J Clin Invest. 2005 (in press)

Marcjeselli et al. (2003). Novel docosanoids inhibit brain ischemia-reperfusion-mediated leukocyte infiltration and pro-inflammatory gene expression. Biol. Chem. 278(44): 43807-17.

Meydani (1990) Dietary modulation of cytokines and biological functions. Nutrition Reviews 48:361-367.

Mukherjee et al. (2004). Neuroprotectin D1: a docosahexaenoic acid-derived docosatriene protects human retinal pigment epithelial cells from oxidative stress. Proc Natl Acad Sci USA. 101(22):8491-6.

Rodriguez and Spur (2004) First total synthesis of 7(S), 16(R),17(S)-Resolvin D2, a potent anti-inflammatory lipid mediator. Tetrahedron Letters 45:8717-8720.

Rodriguez and Spur (2005) First total synthesis of 7(s),17(S)-Resolvin D5, a potent anti-inflammatory docosanoid. Tetrahedron Letters 46(21): 3623-7.

Rorrer et al. (1996). Development and bioreactor cultivation of a novel semidifferentiated tissue suspension derived from the marine plant *Acrosiphonia coalita*. Biotechnology and Bioengineering 49:559-567.

Rorrer et al. (1997). Production of hydroxyl fatty acids by cell suspension cultures of the marine brown alga *Laminaria saccharina*. Phytochemistry 46(5):871-877.

Serhan et al. (2004a). Resolvins, docosatrienes, and neuroprotectins, novel omega-3-derived mediators, and their endogenous aspirin-triggered epimers. Lipids. 39(11):1125-32.

Serhan et al. (2004b). Resolvins, docosatrienes, and neuroprotectins, novel omega-3-derived mediators, and their aspirin-triggered endogenous epimers: an overview of their protective roles in catabasis. Prostaglandins Other Lipid Mediat. 73(3-4):155-72.

Simopoulos (2002). Omega-3 fatty acids in inflammation and autoimmune diseases. J Am Coll Nutr 21(6): 495-505.

Ye et al (2002). Cytochrome P-450 epoxygenase metabolites of docosahexaenoate potently dilate coronary arterioles by activating large-conductance calcium-activated potassium channels. J Pharmacol Therapeut 303(2): 768-76.

U.S. Patent Publication No. 2006/0241088, filed Nov. 21, 2005.

U.S. Provisional Application Ser. No. 60/629,842, filed Nov. 19, 2004.

U.S. Provisional Application Ser. No. 60/729,038, filed Oct. 21, 2005.

U.S. Provisional Application Ser. No. 60/763,964, filed Jan. 31, 2006.

Each reference described or cited herein is incorporated herein by reference in its entirety.

While various embodiments of the present invention have been described in detail, it is apparent that modifications and adaptations of those embodiments will occur to those skilled in the art. It is to be expressly understood, however, that such modifications and adaptations are within the scope of the present invention, as set forth in the following claims.

What is claimed is:

1. An isolated trihydroxy oxylipin of stearidonic acid (SDA) having one hydroxyl group at three of the SDA carbons selected from the group consisting of C6, C7, C9, C10, C12, C13, C15 and C16 of SDA.

2. An isolated dihydroxy oxylipin of stearidonic acid (SDA), wherein the oxylipin is an R- or S-epimer or an R/S epimer of 6,13-dihydroxy SDA or 6,16-dihydroxy SDA or a salt thereof.

3. An isolated monohydroxy oxylipin of stearidonic acid (SDA), wherein the oxylipin is an R- or S-epimer of an oxylipin selected from the group consisting of: 6-hydroxy SDA, 12-hydroxy SDA, and 16-hydroxy SDA or a salt thereof.

4. A composition comprising at least one oxylipin selected from the group consisting of a trihydroxy oxylipin of SDA having one hydroxyl group at three of the SDA carbons selected from the group consisting of C6, C7, C9, C10, C12, C13, C15 and C16 of SDA, an R- or S-epimer of a trihydroxy oxylipin of SDA having one hydroxyl group at three of the SDA carbons selected from the group consisting of C6, C7, C9, C10, C12, C13, C15 and C16 of SDA, an R/S epimer of 6,13-dihydroxy SDA, an R/S epimer of 6,16-dihydroxy SDA, 6-hydroxy SDA, 12-hydroxy SDA, 16-hydroxy SDA and a salt thereof and
a compound selected from the group consisting of: stearidonic acid, γ-linolenic acid, docosapentaenoic acid (C22:5n-6), docosapentaenoic acid (C22:5n-3), docosatetraenoic acid (C22:4n-6), docosahexaenoic acid, eicosapentaenoic acid, an oxylipin derivative of stearidonic acid, an oxylipin derivative of γ-linolenic acid, an oxylipin derivative of docosapentaenoic acid (C22:5n-6), an oxylipin derivative of docosapentaenoic acid (C22:5n-3), an oxylipin derivative of docosatetraenoic acid (C22:4n-6), an oxylipin derivative of docosahexaenoic acid, and an oxylipin derivative of eicosapentaenoic acid.

5. The composition of claim 4, wherein the composition is a therapeutic composition, a nutritional composition, or a cosmetic composition.

6. The composition of claim 4, further comprising aspirin.

7. The composition of claim 4, further comprising at least one agent selected from the group consisting of: a statin, a non-steroidal anti-inflammatory agent, an antioxidant, and a neuroprotective agent.

8. The composition of claim 4, wherein the composition comprises an oil selected from the group consisting of a microbial oil, a plant seed oil, and an aquatic animal oil.

9. An isolated dihydroxy oxylipin of stearidonic acid (SDA), wherein the oxylipin is an R- or S-epimer or an R/S epimer of 6,13-dihydroxy SDA, or a salt thereof.

10. An isolated dihydroxy oxylipin of stearidonic acid (SDA), wherein the oxylipin is an R- or S-epimer or an R/S epimer of 6,16-dihydroxy SDA, or a salt thereof.

11. An isolated monohydroxy oxylipin of stearidonic acid (SDA), wherein the oxylipin is an R- or S-epimer of 6-hydroxy SDA, or salt thereof.

12. An isolated monohydroxy oxylipin of stearidonic acid (SDA), wherein the oxylipin is an R- or S-epimer of 12-hydroxy SDA, or salt thereof.

13. An isolated monohydroxy oxylipin of stearidonic acid (SDA), wherein the oxylipin is an R- or S-epimer of 16-hydroxy SDA, or salt thereof.

* * * * *